United States Patent [19]
Thorpe

[11] Patent Number: 5,474,765
[45] Date of Patent: Dec. 12, 1995

[54] PREPARATION AND USE OF STEROID-POLYANIONIC POLYMER-BASED CONJUGATES TARGETED TO VASCULAR ENDOTHELIAL CELLS

[75] Inventor: Philip E. Thorpe, Dallas, Tex.

[73] Assignee: UT SW Medical CTR at Dallas, Dallas, Tex.

[21] Appl. No.: 856,018

[22] Filed: Mar. 23, 1992

[51] Int. Cl.$^6$ .............................. C08L 5/12; B61K 31/74
[52] U.S. Cl. .................................. 424/178.17; 424/78.27; 536/64; 436/532; 436/533
[58] Field of Search ............................. 424/78.17, 78.18, 424/78.27; 436/532, 533; 536/64; 514/55, 56

[56] References Cited

U.S. PATENT DOCUMENTS

| | | |
|---|---|---|
| 4,771,042 | 9/1988 | Braughler et al. . |
| 4,925,678 | 5/1990 | Ranney .................... 424/493 |
| 4,994,443 | 2/1991 | Folkman et al. .......... 514/56 |
| 5,001,116 | 3/1991 | Folkman et al. .......... 514/56 |
| 5,108,759 | 3/1992 | Ranney .................... 424/493 |
| 5,137,877 | 8/1992 | Kaneko et al. ........... 514/25 |
| 5,155,215 | 10/1992 | Ranney .................... 534/16 |
| 5,213,788 | 5/1993 | Ranney .................... 424/9 |
| 5,260,050 | 11/1993 | Ranney .................... 424/9 |
| 5,336,762 | 8/1994 | Ranney .................... 534/16 |

FOREIGN PATENT DOCUMENTS

| | | |
|---|---|---|
| 0247156 | 6/1993 | European Pat. Off. . |
| 0352295 | 6/1993 | European Pat. Off. . |
| 83/00150 | 1/1983 | WIPO . |
| 90/15816 | 12/1990 | WIPO . |

OTHER PUBLICATIONS van Rijn et al., "Selective Binding of Heparina to Human Endothelial Cells. Implications for Pharmacokinetics" *Thrombosis Research*, 45(3):211–222, 1987.

Barzu et al., "Endothelial Binding Sites for Heparin," *Biochemical Journal*, 238:847–854, 1986.

Barzu et al., "Binding and Endocytosis of Heparin by Human Endothelial Cells in Culture," *Biochimica et Biophysica Acta*, 845:196–203, 1985.

Mahadoo et al., "Vascular Sequestration of Heparin," *Thrombosis Research*, 12(1):79–90, 1977.

Hiebert & Jaques, "The Observation of Heparin on Endothelium After Injection," *Thrombosis Research*, 8(2):195–204, 1976.

Danishefsky, "Synthesis and Properties of Heparin Derivatives," In 'Heparin: Structure, Function and Clinical Implications', Proceedings of the International Symposium, St. Louis, May 1974, R. A. Bradshaw & S. Wesster, Eds., Plenum Press, New York & London, 1975, pp. 105–118.

(List continued on next page.)

*Primary Examiner*—Gollamudi Kishore
*Assistant Examiner*—Peter F. Kulkosky
*Attorney, Agent, or Firm*—Arnold, White & Durkee

[57] ABSTRACT

This invention discloses new targeted conjugates for the delivery of a compound, and particularly, a steroid, to vascular endothelial cells. The conjugates comprise two components, preferably linked by a selectively-hydrolyzable bond, such as an acid-labile bond or enzyme-sensitive bond. The first component, a polyanionic polymer, and preferably, a polysulphated polymer such as a heparin-derivative, specifically directs the conjugate to vascular endothelial cells. The second component is a selected agent, such as asteroid, which exerts a specific effect on the target cell following its release. In particular, the present invention provides novel conjugated angiogenesis inhibitors, for use in the treatment of pathogenic conditions including cancer, arthritis, and diabetic blindness. An inhibitor comprising a heparin derivative and the anti-angiogenic steroid, cortisol, is herein shown to be markedly acid-labile, to suppress DNA synthesis and cell migration in human umbilical vein endothelial cells, to retard or abolish (depending on the route of injection) the vascularization of sponges in vivo and to retard lung tumor growth in mice by 65%. No adverse effects of the conjugate were detected, and equivalent treatments with a mixture of heparin plus cortisol were significantly less effective in all cases.

24 Claims, 14 Drawing Sheets

OTHER PUBLICATIONS

Danishefsky & Siskovic, "Conversion of Carboxyl Groups of Mucopolysacchaides into Amides of Amino Acid Esters," *Carbohydrate Research,* 16:199–205, 1971.

Trouet et al., "A Covalent Linkage Between Daunorubicin and Proteins that is Stable in Serum and Reversible by Lysosomal Hydrolases, as Required for a Lysosomotopic Drug–Carrier Conjugate: In Vitro and In Vivo Studies," *Proceedings of the National Acadamy of Sciences U.S.A.,* 79:626–269, 1982.

Benrezzak et al., "Evaluation of Cortisone–Heparin and Cortisone–Maltose Tetrapalmitate Therapies Against Rodent Tumors. I. Biological Studies," *Anticancer Research,* 9:1883–1888, 1989.

Folkman et al., "Control of Angiogenesis with Synthetic Heparin Substitutes," *Science,* 243:1490–1493, 1990.

Sakamoto & Tanaka, "Mechanism of the Synergistic Effect of Heparin and Cortisone Against Angiogenesis and Tumor Growth," *The Cancer Journal,* 2(1):9–13, 1988.

Sakamoto et al., "Inhibitory Effects of Heparin Plus Cortisone Acetate on Endothelial Cell Growth Both in Cultures and in Masses," *Journal of the National Cancer Institute,* 78(3):581–585, 1987.

Ingber et al., "A Possible Mechanism for Inhibition of Angiogenesis by Angiostatic Steroids: Induction of Capillary Basement Membrane Dissolution," *Endocrinology,* 119(4):1768–1775, 1986.

Crum et al., "A New Class of Steroids Inhibits Angiogenesis in the Presence of Heparin or a Heparin Fragment," *Science,* 230:1375–1378, 1985.

Folkman et al., "Angiogenesis Inhibition and Tumor Regression Caused by Heparin or a Heparin Fragment in the Presence of Cortisone," *Science* 221:719–725, 1983.

Pino, "Binding and Endocytosis of Heparin–Gold Conjugates by the Fenestrated Endothelium of the Rat Choriocapillaris," *Cell Tissue Research,* 250:257–266, 1987.

Bjornsson et al., "Effects of N–Deacetylation and N–Desulfation of Heparin on its Anticoagulant Activity and in Vivo Disposition," *Jrnl. Pharmacol. and Exp. Therapeut.,* 245:804–808, 1988.

International Search Report, mailed Jul. 22, 1993.

Fenselau & Adams, "Heparin Conjugates: Novel Antiangiogenic Agents For Possible Use In Retinopathy Treatment," Invest. Ophtamol. Visual. Sci 29:403, Abstract No. 7, 1988.

Jacobs & Wan Kim, "In Vitro Bioactivity of a Synthesized Prostaglandin $E_1$–Heparin Conjugate," *Journal of Pharmaceutical Science,* 75(2): 172–175, 1986.

LeBaron et al., "Binding of Heparan Sulfate to Type V Collagen: A Mechanism of Cell Substrate Adhesion," *The Journal of Biological Chemistry,* 264(14): 7950–7956, 1989.

Pasternak et al., "Macromolecular Naloxone: A Novel Long–Acting PolymerBound Drug," *Life Science,* 18(9), 976–981, May 1, 1976.

Spare et al., "Controlled Release from Glycosaminoglycan Drug Complexes," In Controlled Release Delivery Systems, Marcel Dekker, Inc. New York, 1983, pp. 107–119.

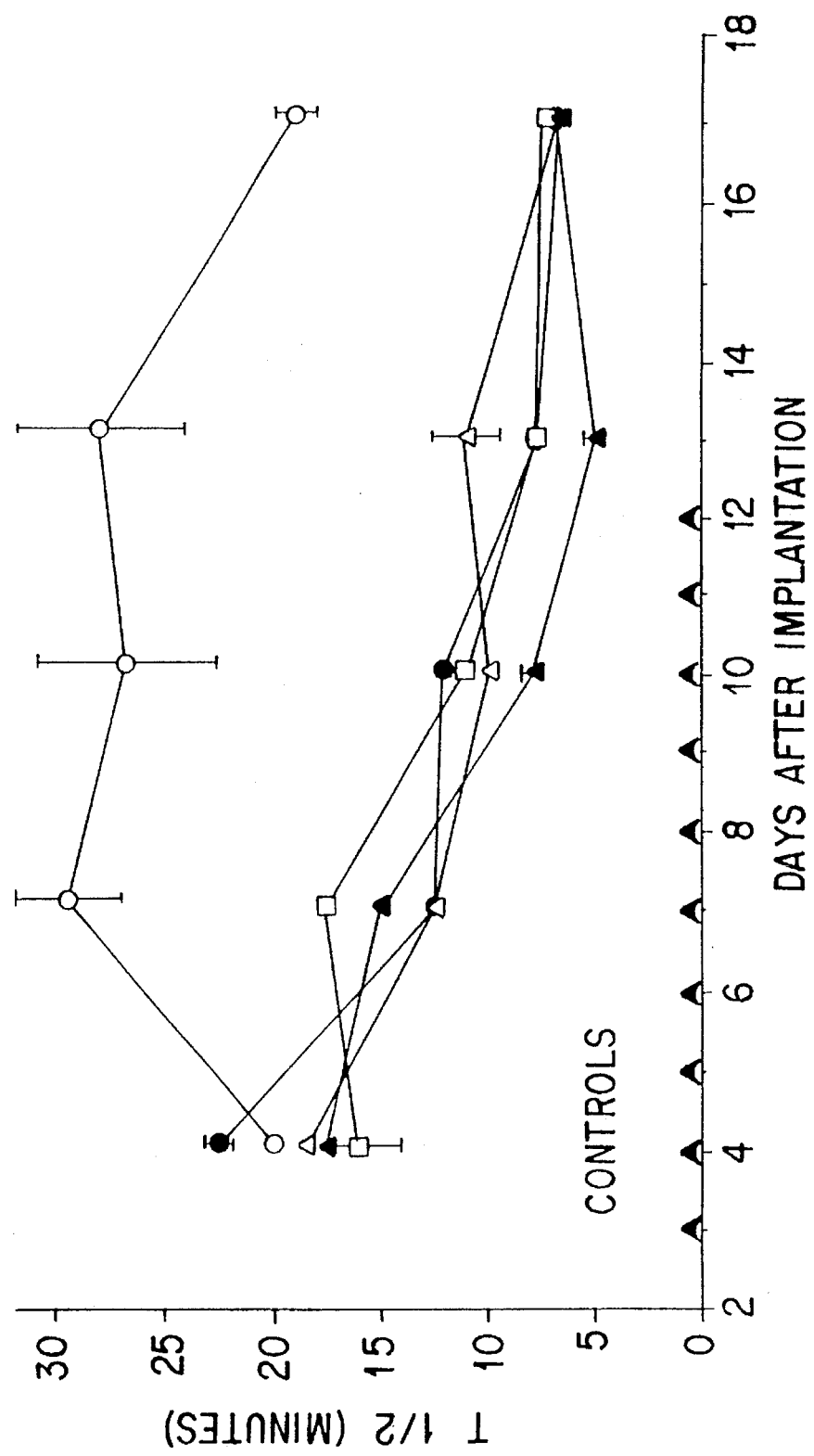

PREPARATION AND USE OF STEROID-POLYANIONIC POLYMER-BASED CONJUGATES TARGETED TO VASCULAR ENDOTHELIAL CELLS

The government owns certain rights in the present invention pursuant to NIH grant No. CA-54168.

BACKGROUND OF THE INVENTION

1. Field of the Invention

The present invention provides novel conjugates for use in targeting a selected agent, and particularly, asteroid, to vascular endothelial cells. These conjugates comprise two components preferably linked by a selectively-hydrolyzable bond, such as an acid-labile bond. Firstly, a polyanionic polymer which directs the conjugate to vascular endothelial cells, and secondly, a selected agent, such as asteroid, which exerts its action following cellular release. In certain aspects, the invention provides novel conjugates that function as targeted angiogenesis inhibitors that are proposed for use in the treatment of pathological conditions such as cancer, arthritis, and diabetic blindness. Preferred inhibitors are those in which the polyanionic polymer is a polysulfated polymer such as a heparin derivative, conjugated to asteroid with anti-angiogenic activity, such as cortisol, or derivatives and variants thereof.

2. Description of the Related Art

The control of endothelial cell proliferation is a vital part of normal homeostatic mechanisms. A disturbance in this process can result in, for example, excessive or inappropriate endothelial cell proliferation or activation which is often associated with disease processes. For example, the proliferation of vascular endothelial cells is vital to angiogenesis, the formation of new blood vessels, which in turn, is associated with many disabling or life-threatening disorders. These include cancer (Algire et al., 1945; Tannock, 1968; Folkman, 1972) and other pathological conditions such as diabetic retinopathy, atherosclerosis, rheumatoid arthritis, synovitis, psoriasis, dermatitis, endometriosis, encephalitis and tonsillitis (Brown & Weiss, 1988, Waltman et al., 1978; Gartner & Henkind, 1978; Moses & Langer, 1991). It is known that angiogenesis rarely occurs in healthy adult humans except during wound healing and during phases of the female reproductive cycle (Hobson & Denekamp, 1984).

In solid tumors, vascular endothelial cells divide about 35 times more rapidly than those in normal tissues, except the uterine epithelium (Denenkamp & Hobson, 1982). Such inappropriate proliferation is necessary for tumor growth and metastasis (Folkman, 1986). Vascular endothelial cell growth and division is also important in chronic inflammatory diseases such as rheumatoid arthritis, psoriasis and synovitis, where these cells proliferate in response to growth factors released within the inflammatory site (Brown & Weiss, 1988). In atherosclerosis, formation of the atherosclerotic plaque is triggered by a monoclonal expansion of endothelial cells in blood vessels (Alpern-Elran et al., 1989). Furthermore, in diabetic retinopathy, blindness is thought to be caused by basement membrane changes in the eye, which stimulate uncontrolled angiogenesis and consumption of the retina (West & Kumar, 1988).

Endothelial cells are also involved in graft rejection. In allograft rejection episodes, endothelial cells express proadhesive determinants that direct leukocyte traffic to the site of the graft. It is believed that the induction of leukocyte adhesion molecules on the endothelial cells in the graft may be induced by locally-released cytokines, as is known to occur in an inflammatory lesion.

As endothelial cells are involved in a wide variety of processes, it has been reasoned that drugs targeted to such cells may be of wide-ranging use clinically. Perhaps most importantly, angiogenesis inhibitors could potentially be of use in the treatment of those diseases, mentioned above, whose pathogenesis is influenced or maintained by the proliferation of vascular endothelial cells. Angiogenesis inhibitors would be particularly advantageous in the treatment of cancer, in which one of the current major problems is the emergence of drug-resistant malignant cells.

Within the last decade, several inhibitors of angiogenesis have been identified (Langer et al., 1976; Taylor & Folkman, 1982; Sharpe et al., 1990, Good et al., 1990, Ingber et al., 1990). For example, anti-angiogenic therapy, in the form of oral or subcutaneous administration of heparin and the steroid cortisone, has been reported to have an anti-tumor effect in mice bearing established tumors of various types (Folkman et al., 1983). It was believed that the heparin, or heparin metabolites, acted together with the cortisone to inhibit angiogenesis and tumor growth. Unfortunately, the magnitude of the anti-tumor effect varied with the batch of heparin used, and later studies from several laboratories have subsequently reported no (Ziche et al., 1985; Penhaligon & Campejohn, 1985), or only modest (Sakamoto et al., 1986; Benrezzak, 1989), anti-tumor effects.

The mechanism underlying the additive anti-angiogenic activity of heparin and cortisone has not been positively identified, although it may be related to the fact that the mixture increases the rate of dissolution of the basement membrane beneath newly formed capillaries (Ingber et al., 1986). Structure-activity studies have shown that steroids lacking glucocorticoid and mineralocorticoid activity can act in conjunction with heparin to inhibit angiogenesis. These studies have led to the description of a new biological activity of steroids, called the angiostatic activity (Crum et al., 1985).

More recently, the synthetic heparin substitute, β-cyclodextrin tetradecasulfate, was reported to augment the anti-angiogenic effects of angiostatic steroids on corneal neovascularization in rabbits when applied locally or topically (Folkman et al., 1989). It was suggested that the β-cyclodextrin tetradecasulfate might act by forming a non-covalent complex with the steroid and promote its binding to the surface of endothelial cells.

Other potential uses of modulating endothelial cell activity include the treatment of inflammatory responses or the stimulation of growth and proliferation. In the latter instance, this would prove useful in stimulating blood vessel growth, for example, in wound repair after accidental injury or surgery, or in promoting the healing of gastrointestinal lesions such as ulcers. Again, various steroids have potential for use in this area.

The clinical use of many agents, including steroids, whether designed to be inhibitory or stimulatory, is often limited by their side effects and toxicities. For example, steroids are known to have negative effects on bone and lymphoid tissues, which can reduce their overall dosages and their therapeutic effectiveness. In particular, steroid treatment is known to be associated with osteoporosis and immunosuppression. Naturally, these are serious drawbacks which currently limit the use of steroids in the treatment of human disorders. Most toxicity can generally be attributed to a lack of selective action, i.e. it is due to the tendency of the drug to exert its effects on cells indiscriminately.

Accordingly, there is currently a substantial need for an improved means of treating diseases or processes involving endothelial cells, and particularly, processes involving inappropriate endothelial cell growth or proliferation. Furthermore, there is a particular need for this means of treatment to have increased selectivity and specificity, allowing the advantageous use of various agents whilst limiting any toxicity of the agents on tissues other than the endothelial cell tissue.

SUMMARY OF THE INVENTION

The present invention seeks to overcome these and other drawbacks inherent in the prior art by providing novel endothelial cell-targeted conjugates for the delivery of a selected agent, such as asteroid, to vascular endothelial cells. The targeting component of the conjugate is a polyanionic polymer, and preferably a polysulfated polymer such as a heparin derivative, which is preferably linked to the selected agent by a selectively-hydrolyzable bond, for example, an acid-labile bond. The selected agent, preferably asteroid, exerts its action on the target cells following release. In certain aspects, the present invention provides conjugates that function as targeted inhibitors of angiogenesis, for use in the treatment of pathological conditions such as cancer, arthritis, and diabetic retinopathy. Particularly preferred inhibitors are those in which a heparin derivative is conjugated to a steroid with anti-angiogenic activity, such as cortisol, and derivatives and variants thereof.

A key aspect of the present invention is the creation of an "endothelial cell-targeted conjugate". The term "endothelial cell-targeted conjugate", as used herein, indicates that the conjugate selectively binds to vascular endothelial cells as opposed to other cell types except the cells of the reticuloendothelial system. "Targeting" of a compound in this manner is intended to refer to, not only the process by which the compound recognizes and binds to specific components of vascular endothelial cells, but also to its uptake by such cells.

The "targeting component" of these novel conjugates is the component that directs the conjugate to its intended site of action, i.e. to vascular endothelial cells. The targeting component therefore controls the biodistribution of the conjugate, and as such, may be considered as a delivery vehicle for the selected agent of the conjugate. Targeting components of the present invention are defined in a general sense as polyanionic polymers, and more particularly, as polysulfated polymers.

It is contemplated that both synthetic as well as naturally occurring polyanionic polymers will be useful in this regard. Of course, where administration of the conjugate to a human is contemplated, one will desire to ensure that the polymer employed is biocompatible, i.e. that it does not cause any substantial adverse effects when administered to a human subject. Virtually all naturally occurring polysulfated polyanions will be suitable in this regard.

Exemplary polymers useful in accordance with this invention will include both N- and O-sulfated polyanionic polysaccharides. Of these, the polysaccharides having free carboxyl groups are considered to be particularly useful because the carboxyl group can serve as a convenient attachment point for drugs and intermediate spacer groups. Such carboxyl-containing sulfated polysaccharides include heparin, heparan sulfate, chondroitin sulfate, dermatan sulfate, sulfated alginic acid and the like. However, a wide variety of naturally-occurring and synthetic N- and O-sulfated polyanionic polysaccharides lacking carboxyl groups could also be used in accordance herewith. These include polymers such as keratan sulfate, dextran sulfate, sulfated cyclodextrins, sulfated chitin, sulfated chitosan, pentosan polysulfate and the like. Each of the foregoing, whether N- or O-sulfated, can be derivatized to introduce functional groups that can serve as attachment points for drugs, other selected agents, or intermediate spacer groups.

In addition to the polysaccharide-based polymers such as those described above, it is contemplated that a variety of synthetic organic polymers will also prove to be employable in the creation of a targeted conjugate. For example, it is contemplated that polysulfated or polysulfonated polymers such as polystyrene sulfonate, sulfated polyvinyl alcohol, polyvinyl sulfate or even polyethylene sulfonate could be employed in place of the more preferred polysaccharides and nonetheless obtain a useful conjugate in accordance with the present invention. As with the polysaccharides, it will generally be preferred to employ polyanionic polymers wherein the negatively charged moieties are sulfate or sulfonate groups. However, it is proposed that other negatively charged groups may be incorporated onto the polymer backbone, such as phosphate, or even carboxyl groups, and that such groups will suffice to achieve some degree of selective targeting.

As mentioned above, in certain preferred embodiments, the inventor contemplates the use of heparin as the targeting component of a given conjugate because it is readily available, relatively inexpensive, its chemistry and medicinal properties have been extensively studied. In preferred embodiments, it is contemplated that a non-anticoagulating derivative of heparin will be used. One of the physiological roles of heparin is to act as an anticoagulant, i.e. to inhibit the clotting reactions of the blood. A non-anticoagulating derivative is therefore a compound devoid or virtually devoid of this activity. The absence of anti-coagulant activity from the conjugate is considered to be advantageous as it will not perturb the physiological reactions occurring in the recipient, and hemorrhage is unlikely to be a problem with heparin-steroid treatment.

Heparin can be converted to a virtually non-anticoagulating form during the novel conjugation procedure described herein. The anti-coagulating activity of heparin is known to be associated in part with the carboxyl groups of the molecule, or more exactly, with the carboxyl groups of the glucuronic or iduronic residues within the heparin structure. These are precisely the groups that are modified on the initial derivatization of heparin to obtain a heparin hydrazide. Therefore, the modification of some or all of the heparin carboxyl groups is advantageous in two respects: it provides the platform for further condensation reactions to create a heparin conjugate, and it renders the heparin derivative virtually devoid of anti-coagulating activity.

It is contemplated that heparin conjugates prepared in accordance with preferred embodiments of the present invention will have less than 2.5%, and preferably, less than 1% of the anticoagulating activity of native (unmodified) heparin. A standard method for use in measuring the anti-coagulant activity of a compound is to determine its ability to inhibit the coagulation of human plasma induced by Russell's viper venom. To conduct an assay of this kind, one would prepare a solution of the test compound in a suitable buffer, such as phosphate-buffered saline (PBS), and mix with fresh citrated human plasma at 37° C. in glass tubes. After a short period of time, such as 1 minute, one would add Russell's viper venom (e.g., Sigma# RVCL-1) to the tube and mix. After a short period of time, such as 15 seconds, prewarmed CaCl$_2$ solution should be added, the contents mixed incubated at 37° C., and the time taken for the plasma to clot determined. To calculate the % anticoagulant activity of a heparin derivative or conjugate, one would compare the clotting time for plasma treated with that compound to the clotting time for plasma treated with native (unmodified) heparin which would, by definition, be 100%.

The sulfate groups of the heparin molecule have been determined to be important for the tight binding of heparin derivatives to vascular endothelial cells. Therefore, a further aspect of this invention is to create a heparin conjugate in which the heparin derivative has one or more unmodified sulfate residues, i.e. a heparin derivative in which one or more of the naturally-occurring sulfate residues remain unchanged during the preparation of the conjugate. The conjugation procedure described herein is conducted so that the sulfate residues remain unaltered and can direct the binding of the conjugate to the sulfated polyanion receptors.

It is not believed to be necessary to routinely determine the ability of a targeted conjugate to bind to vascular endothelial cells during its construction, so long as one does not radically modify the sulfate groups of the molecule. However, if desired, one could examine this property, for example, by conducting a binding assay. To conveniently perform such an assay, one would label the conjugate, for example with a radiolabel, and determine its ability to bind to vascular endothelial cells in culture, such as human umbilical vein endothelial (HUVE) cells. This would be achieved by incubating the cells with the conjugate in a medium to allow binding, removing any unbound conjugate by washing, and then measuring the cell-associated label, i.e. the cell-associated radioactivity. One could compare the binding of the test conjugate with that of native targeting molecule, for example, heparin.

Various selected agents are proposed to be of use in accordance herewith. The term "selected agent" is used herein simply to refer to the component of the conjugate, other than the targeting component, which is delivered to the endothelial cells by the targeting component. Possible selected agents include radioisotopes, drugs which inhibit or promote DNA synthesis, drugs which suppress or enhance gene transcription, drugs which affect cell surface functions and, indeed, any agent that one may wish to target to an endothelial cell. Pharmacological agents considered to be of particular use include those which, for example, are known to either stimulate or inhibit cellular proliferation. Pharmacological agents of this kind include ionophores, antimetabolites, autacoids, vinca alkaloids, epipodophyllotoxins, alkylating agents, antibiotic chemotherapeutic agents (see Table I), and in preferred embodiments, steroids, which are considered to be particularly useful as selected agents in conjugates of the present invention.

In important embodiments, the present invention provides conjugates that function as inhibitors of angiogenesis, i.e. that act to inhibit the growth of blood vessels. In such conjugates, one would naturally choose to use a pharmacological agent with anti-angiogenic activity, such as a steroid. It is contemplated that suitable steroids for use in these embodiments include those in Table II. In certain embodiments, the steroid cortisol is preferred because it is inexpensive, is straightforward to conjugate to heparin derivatives, and, when thus conjugated, efficiently inhibits angiogenesis.

TABLE I

CHEMOTHERAPEUTIC AGENTS

| Class | Type of Agent | Nonproprietary Names (Other Names) |
|---|---|---|
| Alkylating Agents | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines and Methylmelamines | Hexamethylmelamine |
| | | Thiotepa |
| | Alkyl Sulfonates | Busulfan |
| | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; dimethyltriazenoimidazolecarboxamide) |
| Antimetabolites | Folic Acid Analogs | Methotrexate (amethopterin) |
| | Pyrimidine Analogs | Fluorouracil (5-fluorouracil; 5-FU) |
| | | Floxuridine (fluorodeoxyuridine; FUdR) |
| | | Cytarabine (cytosine arabinoside) |
| Antimetabolites continued | Purine Analogs and Related Inhibitors | Mercaptopurine (6-mercaptopurine; 6-MP) |
| | | Thioguanine (6-thioguanine; TG) |
| | | Pentostatin (2'-deoxycoformycin |
| Natural Products | Vinca Alkaloids | Vinblastine (VLB) |
| | | Vincristine |
| | Epipodophyllotoxins | Etoposide |
| | | Teniposide |
| | Antibiotics | Dactinomycin (actinomycin D) |
| | | Daunorubicin (daunomycin; rubidomycin) |
| | | Doxorubicin |
| | | Bleomycin |
| | | Plicamycin (mithramycin) |
| | | Mitomycin (mitomycin C) |
| | Enzymes | L-Asparaginase |
| | Biological Response Modifiers | Interferon alpha |
| Miscellaneous Agents | Platinum Coordination Complexes | Cisplatin (cis-DDP) |
| | | Carboplatin |
| | Anthracenedione | Mitoxantrone |
| | Substituted Urea | Hydroxyurea |
| | Methyl Hydrazine Derivative | Procarbazine (N-methylhydrazine, MIH) |
| | Adrenocortical Suppressant | Mitotane (o,p'-DDD) |
| | | Aminoglutethimide |

TABLE II

STEROIDS* FOR USE IN TARGETED ANGIOGENESIS INHIBITORS

| | |
|---|---|
| Tetrahydrocorticosterone | Tetrahydrocortexolone |
| Cortisol (hydrocortisone) | Prednisone |
| Tetrahydrocortisol | Triamcinolone |
| 11 α-epihydrocortisol | Alclometasone |
| Cortisone | Amcinonide |
| Tetrahydrocortisone | Clobetasol |
| Corticosterone | Clobetasone |
| Deoxycorticosterone | Clocortolone |
| Cortexolone | Desonide |
| Beclomethasone dipropionate | Desoximetasone |
| Betamethasone | Diflorasone |
| Dexamethasone | Fluocinolone acetonide |
| Flunisolide | Fluocinonide |
| Methylprednisolone | Fluorometholone |
| 17 α-hydroxyprogesterone | Fluocortolone |
| Tetrahydro S | Flurandrenolide |
| Paramethasone | Halcinonide |
| Prednisolone | Medrysone |
| Pregnenolone | Mometasone |

*Plus derivatives thereof, such as the 21-phosphate, 21-hemisuccinate, 21-valerate, 21-sulfate derivatives.

The term anti-angiogenic (or angiostatic) steroid arose following studies on steroids lacking significant glucocorticoid and mineralocorticoid activity that inhibited angiogenesis under certain conditions. Although useful, it will be appreciated that the creation of anti-angiogenic conjugates in accordance with the present invention is not limited to the use of steroids which are known to lack significant glucocorticoid and/or mineralocorticoid activity. Accordingly, any steroid with proven, or even possible, anti-angiogenic activity may be coupled to heparin to form a conjugate, the anti-angiogenic properties of which can then be examined. Furthermore, as the conjugates are specifically targeted to vascular epithelia, it is contemplated various steroids which have previously been associated with adverse clinical effects may now be used advantageously in the inhibition of angiogenesis.

In other embodiments, the present invention contemplates targeted conjugates that function as promoters of angiogenesis for use in stimulating blood vessel growth. Examples of selected agents or drugs that might be used in this way include phorbol esters, adenosine, inosine, hypoxanthine, nicotinamide, prostaglandin E2, and calcium ionophores such as nimodipine. It is envisioned that such conjugates would be of use in the treatment of conditions and diseases wherein a limited blood supply poses a problem, for example in the treatment of placental insufficiency, or the healing of gastric ulcers, or in the stimulation of wound repair.

The inventor contemplates that the components of the novel conjugates may be linked by a disulfide or trisulfide bond thus: polyanionic polymer-S-S-(S)-selected agent, for example, heparin-S-S-S-calicheamicin. However, in preferred embodiments, the bond between the targeting component and the selected agent of the conjugates will be a selectively-hydrolyzable bond. The term "selectively-hydrolyzable bond" as used herein, refers to a bond which is stable unless exposed to particular conditions, i.e. unless placed within a certain environment or in contact with a particular agent. Such bonds include, for example, acid-labile and enzyme-sensitive bonds. In these cases, the "environment" or "agent" capable of inducing hydrolysis is an acidic pH, and a specific enzyme, respectively. Such selective-release design features allow the conjugates to remain intact whilst in the blood stream or other extracellular environments, and to be hydrolyzed only following binding to, or uptake into, vascular endothelial cells.

In certain embodiments, the selectively-hydrolyzable bond of the conjugate will be an acid-labile bond. As used herein, the term "acid-labile" is intended to refer to a conjugate (or the bond joining the two components of the conjugate) that is hydrolyzed simply by exposure to an acidic environment, and particularly, by exposure to an environment with a pH of 4.8 or lower. Conjugates with a half life of between 10 minutes and 24 hours, and preferably of between 15 minutes and 2 hours, in dilute solutions of 50 mM or less at 20° C. and pH 4.8 are particularly preferred. An accompanying property of such conjugates is their stability at near-neutral pHs. The term "stable at near-neutral pHs" is herein intended to refer to a conjugate that is not substantially hydrolysed at pHs in the range of pH 7.4 to pH 7.6. For example, conjugates having less than 50%, and preferably, less than 10% breakdown after 24 hours in dilute solutions of 50 mM or less at 20° C. and pH 7.4 are also particularly preferred.

A useful method for analyzing the pH stability of a conjugate is to examine its UV spectrum over a pH range. The dissociation of the conjugate is determined by measuring the appearance of free cortisol, which is known to have a maximum at 242 nm. Firstly, the UV spectrum (from 400 nm to 200 nm) of the conjugate in distilled water may be scanned, then the pH of the conjugate solution made more acidic and the UV spectrum repeatedly re-scanned, whilst keeping the temperature constant. The half-life of the decomposition can be calculated as the time for the OD at 274 nm to decay to half its initial value. The % breakdown of the conjugate at a given time can be calculated as the % of free cortisol which has formed over the time period, with time 0 taken as 0% breakdown.

Typical acid-labile linkages believed to be useful in connection with the present invention include those that employ a Schiff's base linkage, for example, linkages incorporating the condensation product of an aldehyde or ketone with a hydrazine, a hydrazide, a primary or secondary amine or their derivatives. A particularly preferred Schiff's base linkage for use in accordance herewith is an acyl hydrazone bond, formed when a hydrazide derivative of heparin, or other polyanionic polymer, is condensed with a selected agent containing a ketone or aldehyde group. It is proposed that the heparin or other polyanionic polymer can be derivatised to introduce hydrazide-terminating side chains of various lengths. The simplest hydrazide-terminating side chain contemplated has the structure:

where

R=polyanionic polymer

Longer hydrazide-terminating side chains are also proposed to be of use, for example, linkers of the formula:

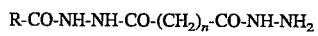

wherein n=1–20 and

R=polyanionic polymer

In preferred embodiments, the inventor contemplates the use of hydrazide linkers that contain from 1 to 4 central $CH_2$ groups, i.e. from n=1 to n=4.

Other possible acid-labile linkages that would be suitable incorporate ortho ester, acetal and ketal functionalities that undergo acid-catalyzed dissociation but are base-stable; and cis-aconitic, maleic, or citraconic acid functionalities having a free carboxyl group juxtaposed to the acid-sensitive amide or ester linkage.

In further embodiments, the selectively-hydrolyzable bond of the conjugate will be an enzyme-sensitive bond. The term "enzyme-sensitive" as used herein, is intended to refer to a conjugate (or the bond joining the two components of the conjugate) that is hydrolyzed by exposure to a specific enzyme. Examples of such bonds include esters, peptides, amides, phosphodiesters, and even glycosidic bonds, which are hydrolysed by exposure to an esterase, protease or peptidase, amidase, phosphodiesterase and glycosidase, respectively. Of course, in designing an enzyme-sensitive bond, one will generally desire to avoid such bonds that could be hydrolysed by exposure to components normally present in the blood stream, such as certain esters.

It is contemplated that the presence of an enzyme-sensitive bond within a conjugate of the present invention may add a further dimension to the utility of the conjugate. In this manner, conjugates could be engineered that are hydrolysed only by exposure to an enzyme known to have a precise cellular location, including enzymes associated with the plasma membrane, the endocytotic vesicles and the lysosomes.

Various side chains of a single polyanionic targeting molecule, such as heparin, can be modified by the addition of a selected agent to create a conjugate in accordance with the present invention. The molar ratios of selected agent to targeting component in a given conjugate can therefore lie between 0.1:1 and 80:1, depending on the particular polymer and selected agent utilized. In embodiments concerning the conjugation of steroids, molar ratios of greater than one, and preferably, of greater than 5:1 are contemplated.

The present invention further provides a method for preparing an endothelial cell-targeted polyanionic polymer conjugate comprising the following steps:

(a) condensing in a reaction mixture the selected polyanionic polymer with a derivatizing agent to form a derivatized polyanionic polymer;

(b) removing from the reaction mixture any unreacted material from said derivatised polyanionic polymer;

(c) adding to the reaction mixture a molar excess of the selected agent to be conjugated; and (d) incubating the reaction mixture to provide a polyanionic polymer-agent conjugate.

In preferred embodiments, the polyanionic polymer used to form the targeting component of the conjugate will be heparin, and even more preferably, it will high molecular weight heparin, e.g. with a molecular weight on the order of 5,000 to 25,000. Particularly preferred derivatizing agents for use in accordance with the above method are hydrazine and hydrazide derivatives. In using such agents for the preparation of a heparin conjugate, the initial step in the procedure is the creation of a heparin hydrazide, using an excess of water soluble carbodiimide, such as EDC, at an acidic pH.

In the preferred mode of synthesis of a conjugate between, for example, heparin and an agent having an available ketone, or aldehyde group, such as asteroid, the initial derivatization can be achieved by carrying out the reaction in a similar manner to that described for the synthesis of heparinylglycine (Danishefsky & Siskovic, 1971). To condense heparin with adipic dihydrazide one would prepare a sample of high molecular weight heparin at an appropriate concentration, such as 10 mg/ml, and add adipic dihydrazide to a final concentration of approximately 0.5M. The pH of the solution should then be adjusted to, for example, about pH 4.75 by the addition of a suitable acid, such as 1M HCl. Next, one would add a freshly prepared solution of EDC (1-ethyl-3-(3-dimethylaminopropyl)-carbodiimide) in water was added to give a final EDC concentration of approximately 10.7 mg/ml, and allow the reaction to proceed at room temperature while maintaining the pH at approximately 4.75 by the periodic addition of, for example, 1M HCl. Following pH stabilization (~2–3 hours), the mixture should be kept at 4° C. for a longer period of time, such as 48 hours, and then dialyzed extensively into 1 mM HCl, for example, using four changes of dialyzate over 4 days. One would then dialyze the mixture into a suitable buffer, such as 0.1M sodium acetate, pH 4.0 and adjust to an appropriate concentration, such as 1 mg/ml.

However, the inventor contemplates that other methods of derivatizing a polyanionic polymer, such as heparin, to permit the subsequent attachment of a selected agent having a free aldehyde or ketone group will also be suitable. For example, the initial derivatization can take advantage of available —COOH groups, such as those of the iduronic or glucuronic acid residues of heparin, as in the following condensation reactions which might, for example, employ a carbodiimide as the condensing agent:

R.COOH+HCO.NH.NH$_2$→R.CO.N

CO.NH.NH$_2$     (a)

where $\vee\vee\vee\vee$ can be any aliphatic or aromatic intermediate grouping, such as $(CH_2)_n$, $(CH_2O)_n$, $(CH_2.CO.NH)_n$, $(CH(OH))_n$ and derivatives thereof, also wherein n=0–20 or so, with n=0–8 being preferred, and n=0–4 being even more preferred.

R.COOH+H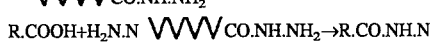CO.NH.NH$_2$→R.CO.

$\vee\vee\vee\vee$CO.NH.NH$_2$     (b)

R.COOH+H$_2$N.N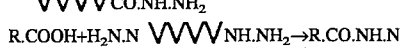CO.NH.NH$_2$→R.CO.NH.N $\vee\vee\vee\vee$CO.NH.NH$_2$     (c)

R.COOH+H$_2$N.N$\vee\vee\vee\vee$NH.NH$_2$→R.CO.NH.N $\vee\vee\vee\vee$NH.NH$_2$     (d)

R.COOH+HNH.NH$_2$→R.CO. $\vee\vee\vee\vee$NH.NH$_2$     (e)

Furthermore, derivatization reactions involving —NH.CO.CH$_3$, are also contemplated to be of use in accordance with the present invention. Such groups can be found on the sugar residues of polyanionic polymers, such as the N-acetylglucosamine groups of heparin. In performing a derivatization reaction of this kind, one would first partially or completely deacetylate such groups, for example, using an acid- or base-catalyzed reaction, or by hydrazinolysis in aqueous hydrazine containing 1% hydrazine sulfate (as represented below).

R.NH.CO.CH$_3$→R.NH$_2$

Selected agents containing, for example, a ketone or aldehyde, a carboxyl group, a sulfonic acid group or derivatives thereof such as carboxylic anhydrides or sulfonyl halides could then be reacted with the amine groups of the polyanionic polymer.

Where polyanionic polymers containing N-sulfated sugars are used as a targeting component, these groups can also be derivatized. Firstly, one would partially or completely de-N-sulfate, for example, using dimethylsulfoxide containing 5% H$_2$O or MeOH at 20° C.–50° C. (as represented below).

R-NH.SO$_3^-$→R-NH$_2$

Selected agents containing, for example, a ketone or aldehyde, a carboxyl group, a sulfonic acid group or derivatives thereof such as carboxylic anhydrides or sulfonyl halides could then be reacted with the amine groups of the polyanionic polymer.

Further derivatizing reactions involving sugars of the polyanionic polymers are also contemplated, for example, those utilizing the OH groups of the sugar residues. As represented below, one method contemplates the use of an anhydride, for example, succinic anhydride, in the first step to introduce a carboxyl group. In the second step, any one of the compounds detailed above in examples (a) to (e) could be condensed with the carboxyl group, for example, hydrazine. Following derivatization according to these steps, the polymer could again be reacted with selected agents containing, for example, an aldehyde or ketone, a carboxylic group, a sulfonic acid group or derivatives thereof such as carboxylic anhydrides or sulfonyl halides.

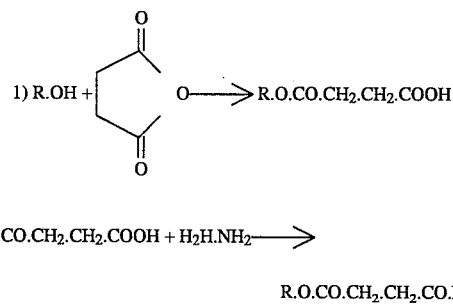

2) R.O.CO.CH$_2$.CH$_2$.COOH + H$_2$H.NH$_2$ ⟶

R.O.CO.CH$_2$.CH$_2$.CO.NH.NH$_2$

To create a covalently bonded heparin-agent conjugate, one would form a reaction mixture by adding a solution of an agent with one or more free aldehyde or ketone groups, such as a steroid, to the heparin-hydrazide to give an appropriate final concentration, for example, in the case of asteroid, of approximately 3 to 4 mg/ml steroid. Incubation of this reaction mixture at a temperature of, for example, between 15° C. and 60° C., leads to the formation of the heparin-steroid conjugate product. A suitable period of time for this incubation is considered to be between approximately 1 hour and 14 days, depending on the reactivity of the steroid. After formation, the product can be stabilized by adjusting the pH to –pH 10 with a suitable alkali, such as 1M NaOH, and then dialyzing extensively into water whose pH has been adjusted to 10. For long-term storage, the dialyzed product can be freeze-dried and placed in a desiccator at 4° C..

It is envisioned that endothelial cell-targeted conjugates prepared in accordance with the present invention may be advantageously used in a number of different embodiments. Importantly, such novel conjugates will have utility in the clinical treatment of a spectrum of human disorders. In its broadest sense, the present invention provides a universally applicable means of targeting any drug or other selected agent to a vascular endothelial cell. Various conjugates can be thus synthesized, using different targeting polymers and selected agents, for use in a wide variety of treatment regimens. A particularly important aspect of the present invention is the use of targeted conjugates as inhibitors of angiogenesis in the treatment of various conditions including cancer, arthritis, and diabetic retinopathy.

In certain embodiments, the present invention concerns a method for introducing asteroid to a vascular endothelial cell. To accomplish this, one would simply prepare an endothelial cell-targeted steroid conjugate, as described above, and allow vascular endothelial cells to be exposed to the conjugate. Related methodological embodiments provide a means for either stimulating or inhibiting DNA synthesis and cellular proliferation in vascular endothelial cells. To achieve these ends, one would again prepare a targeted steroid conjugate, as described above, and expose vascular endothelial cells to the conjugate. Naturally, to stimulate DNA synthesis one would employ a conjugate with an anabolic steroid, and to inhibit DNA synthesis, an anti-angiogenic conjugate should be chosen.

In related methodological embodiments, the present invention provides a means for inhibiting the migration of vascular endothelial cells. To achieve this, one would prepare an endothelial-cell targeted steroid conjugate using asteroid with anti-angiogenic activity, as described herein, and allow vascular endothelial cells to be exposed to the conjugate. The method for assaying cellular migration preferred by the present inventor is the measurement of repair in cultured monolayers wounded by a scarring action. The degree of wound repair is determined in the presence and absence of an endothelial cell-targeted steroid conjugate, and the two values compared. After wounding, the monolayer cultures are incubated at 37° C. for a period sufficient to allow repair, such as 5 days, and their appearance, with and without the conjugate, is compared.

The methods described above are equally applicable to vascular endothelial cells in vitro, for example, in tissue culture, or in vivo. To achieve these effects in cultured endothelial cells, all that is required is to simply add the conjugate to the culture medium. To achieve like effects with endothelial cells in a living animal, one would introduce the targeted steroid conjugate to the animal, where it would be specifically targeted to, and imported by, the vascular endothelial cells. Naturally, where the animal has a disease or a disorder, the administration of a conjugate provides an effective means of treatment. The direct effects of a conjugate on vascular endothelial cells, such as inhibition of DNA synthesis, are more difficult to measure from experiments conducted in vivo. However, several assays are available to analyze the effects on the physiological processes occurring.

One assay which gives an indication of vascular endothelial cell DNA synthesis, proliferation and migration is to examine the vascularization of implanted material, such as a sponge. To prepare an experimental animal (for example, a mouse) for a sponge vascularization experiment, one would implant a sponge disc with an internal cannula into an appropriate site, such as into a subcutaneous pouch, and exteriorize the cannula. To assess vascularization of the sponge, one would anaesthetize the animal, inject a sterile solution of a non-metabolizable labeled compound, such as $^{133}$Xe in saline, into the sponge via the cannula and then plug the cannula to prevent escape of the labeled compound. The radioactivity would then be measured, for example, using a collimated gamma scintillation detector situated 1cm above the sponge.

In an assay of this kind, freshly implanted sponges would be avascular and one would expect the $^{133}$Xe to be cleared slowly. In contrast, in a fully vascularized sponge, the network of blood vessels would lead to rapid clearance. Following injection of a targeted steroid conjugate into the experimental animal, or into the sponge via the cannula, one can thus determine its effect on the vascularization process by measuring the $^{133}$Xe clearance rate. In an experiment of this kind, one can also subsequently dissect out the sponge and obtain transverse frozen sections for direct analysis. For example, one may wish to immuno-identify any blood vessels, and determine their numbers, appearance, and the presence of blood cells within them.

In particularly important embodiments, the present invention contemplates the clinical use of endothelial cell targeted steroid conjugates to treat several human diseases. Clearly, administering a conjugate of the present invention to an animal provides a means for either inhibiting, or stimulating, angiogenesis, i.e. for reducing or increasing the number of blood vessels and the blood supply to an area of the body. Inhibition of angiogenesis is an effective method by which to treat various diseases which are caused or perpetuated by an inappropriate blood vessel growth. Such disease include cancer, rheumatoid arthritis, diabetic retinopathy, atherosclerosis, synovitis, psoriasis, dermatitis, endometriosis encephalitis and tonsillitis. In the treatment of cancer, the administration of a heparin-steroid conjugate also provides a means to inhibit metastasis. Alternatively, the stimulation of angiogenesis would be useful in treating conditions such as placental insufficiency or gastric ulcers, or in the stimulation of blood vessel growth in wound repair. Conjugates of the present invention will also find utility in the control of inflammatory diseases.

The novel conjugates of the present invention may be administered alone or in combination with pharmaceutically acceptable carriers, in either single or multiple doses. Naturally, the pharmacological composition of a conjugate will be dependent on the route of administration chosen, which will in turn, be partly dependent on the condition being treated. The conjugates can be administered by one or more of a variety of routes including injection, topical administration, and release from a biodegradable drug-release capsule. Therefore, the conjugates, or pharmaceutical compositions thereof, can be administered in a variety of dosage forms including, for example, injectable solutions, or encapsulated within a biodegradable polymer which acts as a slow-release capsule.

Suitable pharmaceutical carriers for use in conjunction with the present invention include inert solid diluents or fillers, sterile aqueous solution and various organic solvents, the choice of which will again vary according to the route of administration. For parenteral administration, including intravenous, intramuscular and subcutaneous injection, solutions of the conjugates in various oils, emulsions, or aqueous sterile buffers may be employed. The precise compositions and use of such pharmaceutical carriers will be known to those of skill in the art in light of the present disclosure.

DETAILED DESCRIPTION OF THE PREFERRED EMBODIMENTS

Figure 1:
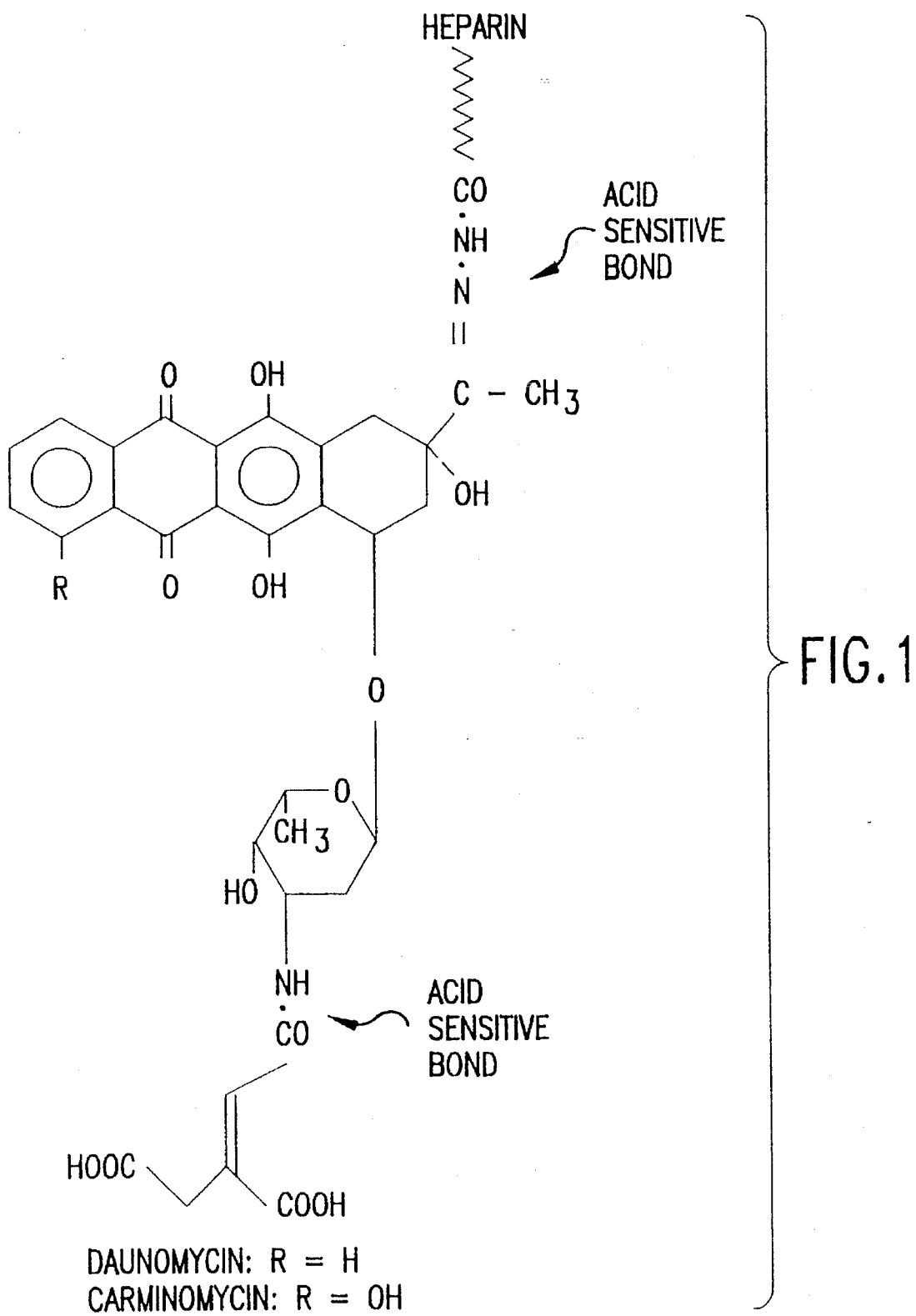
FIG. 1. Structure of heparin-daunomycin and heparin-carminomycin conjugates.

Excessive or inappropriate endothelial cell proliferation or activation can contribute to the cause or maintenance of several disease processes. This includes angiogenesis, the formation of new blood vessels, which is associated with many disabling or life-threatening disorders in adults. Such pathological conditions include cancer, diabetic retinopathy, atherosclerosis, rheumatoid arthritis, synovitis, psoriasis, dermatitis, encephalitis and tonsillitis. Disturbed endothelial cell processes are also involved in inflammatory lesions and graft rejection, where the endothelial cells express proadhesive determinants that direct leukocyte traffic to the area.

As endothelial cells are involved in a wide variety of disorders, drugs targeted to such cells may be of wide-ranging use clinically. For example, angiogenesis inhibitors could be used in the treatment of those diseases, mentioned above, which are at least partially dependent on the aberrant proliferation of vascular endothelial cells. Such inhibitors would be particularly useful in the treatment of cancer, arthritis and diabetic retinopathy.

A variety of pharmacologic agents are known which exhibit anticellular, antiproliferative or anti-inflammatory actions, and could potentially be of use in the treatment of one or more conditions involving epithelial cell growth or activation. Unfortunately, many of these agents, particularly antiproliferative agents, exhibit profound side effects and toxicities which can limit their overall dosages or therapeutic regimens. Most toxicity can be attributed generally to a lack of selective action.

Many toxicities associated with anti-neoplastic therapy can be traced to the relatively non-selective mode or site of action of chemotherapeutic agents presently in use, which rely simply on an increased growth rate of most tumor cells as compared to most normal cells for their selectivity. Drugs such as Ara C, methotrexate, 5-FU, anthracyclines, mitomycin C, alkylating agents, as well as a variety of others, have toxicities attributable to the tendency of the drug to exert its anticellular effect on dividing cells indiscriminately. Similarly, while angiostatic steroids such as cortisol, hydrocortisone, dexamethasone, and the like, are attractive agents for potential use in anti-angiogenic therapy, they induce side effects such as osteoporosis and immunosuppression which reduce their clinical usefulness.

The targeting of drugs to specific sites within the body may be able to reduce their toxic effects on other systems. One approach to the cell specific targeting of drugs has been the formation of antibody-drug conjugates, wherein the antibody directs the associated drug or toxin to a target cell such as a tumor having a cell surface antigen marker. A variety of tumor-directed antibody-drug conjugates have been prepared and tested for use as potential therapeutic agents, such as in the treatment of cancer. However, most drugs conjugated with antibodies, other than immunoconjugates of highly cytotoxic moieties such as ricin A chain molecules, have met with little success. The reason for this is unclear but is likely due to the inability to deliver a sufficient number of drug molecules to the target to be effective, or additionally it could be due to an inability to deliver the drug to the target in an active form, such as a inability to "release" the drug from its conjugate bound form.

Liposomal encapsulation constitutes another means of altering the pharmacologic properties of a drug, including altered biodistribution and reduced toxicity. Liposomal encapsulation involves the incorporation of molecules of the drug into a "capsule" of lipid materials, usually composed of uni- or multilamellar vesicles of various phospholipidso Unfortunately, the ability to form stable liposomes of a particular agent is somewhat limited, in that liposome stability is a function of a variety of parameters such as drug lipophilicity and other structural consideration. Thus, liposomal encapsulation has not proved to be applicable to a broad spectrum of agents. Furthermore, the ability of liposomal encapsulation to alter biodistribution is unpredictable at best. Thus, such encapsulation has not provided a particularly satisfactory broadly applicable means of targeting a selected drug in a uniform, tissue-specific manner.

Accordingly, there has existed in the art a great need for an improved means to treat diseases or processes involving endothelial cells, and particularly, disorders involving endothelial cell growth or proliferation. Because many drugs currently available for treating conditions of cell growth or activation have significant associated toxicities, and are not specific for selected tissues such as endothelial cell tissues, there is a particular need for new or improved drugs having increased selectivity and specificity, and hence, reduced toxicities, for use in the treatment of several human disorders.

The present invention is directed to developing new conjugates for use in targeting a compound or drug to vascular endothelial cells. The conjugates of the present invention were designed to have two components linked by a selectively-hydrolyzable bond, such as an acid-labile or enzyme-sensitive bond. The function of the first component would be to specifically direct the conjugate to the target tissue, i.e. to the vascular endothelial cells. The second component is a selected agent, for example, asteroid, which would exert its effects only on the target cells following its release from the targeting moiety at the cell surface or within intracellular compartments.

The targeting of the novel conjugates specifically to endothelial cells is an important feature of the conjugates. This would enable various selected agents, including steroids, to be used whilst avoiding possible side-effects associated with their action on tissues other than the desired target tissue. This is a common occurrence, for example, the use of steroids is associated with adverse effects on bone metabolism and the immune system.

Compounds considered to be of use in targeting to vascular endothelial cells were naturally occurring and synthetic polyanionic polymers, and more particularly, polysulfated polymers. Polymers of this kind include both N- and O-sulfated polyanionic polysaccharides such as heparin, heparan sulfate, chondroitin sulfate, keratan sulfate, dermatan sulfate, sulfated chitin, sulfated chitosan, sulfated alginic acid, pentosan polysulfate and sulfated cyclodextrins or the like, or synthetic organic polymers such as polystyrene sulfonate, sulfated polyvinyl alcohol, polyvinyl sulfate or polyethylene sulfonate.

In one example, the component chosen to target the conjugates to the vascular epithelium was high molecular weight heparin. It was reasoned that a heparin derivative with intact O- or N-linked sulfate groups would bind to sulfated polyanion (heparin) receptors which are present on vascular endothelial cells (Florey et al., 1959; Hiebert & Jacques, 1976; Mahadoo et al., 1977; Bârzu et al., 1985; 1986; Pino, 1987; Van Rijn et al., 1987) and on cells of the reticuloendothelial system (Schaefer et al., 1980; Stau et al., 1973; Fabian et al., 1978).

The inventor also proposes to utilize a non-anticoagulating derivative of heparin, which would allow the normal clotting actions of the blood to occur. From structure-activity studies, distinct elements within the heparin molecule have been identified as being responsible for its various properties. The anti-coagulating activity has been shown to reside within the carboxyl groups of the first seven sugar moieties. Therefore the inventor proposed to modify such carboxyl groups whilst leaving the sulphate residues intact.

Many agents could be specifically delivered to vascular endothelial cells using a targeting component as described above, including radioisotopes and drugs which inhibit or promote DNA synthesis or gene transcription. Particularly useful agents for conjugation include those which, for example, either stimulate or inhibit cellular proliferation. Pharmacological agents of this kind include ionophores, antimetabolites, autacoids, vinca alkaloids, epipodophyllotoxins, alkylating agents, phorbol esters, prostaglandins, antibiotic chemotherapeutic agents, and in preferred embodiments, steroids, which are considered to be particularly useful as selected agents in the endothelial cell-targeted conjugates of the present invention.

Certain aspects of the present invention are particularly concerned with the creation of novel conjugates that can function as inhibitors of angiogenesis, for use in the treatment of diseases which depend on the inappropriate growth of blood vessels. To create an angiogenesis inhibitor, the inventor first chose an anti-angiogenic steroid, such as cortisol (hydrocortisone). It was reasoned that the steroidal component of the conjugated inhibitor would act to specifically inhibit the proliferation of the vascular endothelial cells, without otherwise damaging them. For example, cortisol would inhibit DNA synthesis, by altering gene transcription, and thereby suppress cell division.

Because steroids are known to exert their effects on cellular events by influencing gene transcription (Haynes, 1990) they have the potential to cause many unwanted disruptions to various processes in other cell types. By targeting the steroids specifically to vascular endothelia, the present invention provides a means for limiting their effects specifically to such cells. Any undesirable effects on other tissues, such as bone and lymph, would be minimized by their limited exposure to the compound. In the case of the inhibitors, it was contemplated that dividing vascular endothelial cells may also preferentially bind and endocytose more of the conjugate, as had been observed for unconjugated heparin (Sakamoto & Tanaka, 1988).

The bond joining the two components of these novel targeted conjugates was designed to be a selectively-hydrolyzable bond, such as an acid-labile or enzyme-sensitive bond. It was reasoned that the presence of such a bond would allow the generally-stable conjugate to be hydrolysed only under certain conditions, such as on exposure to an acidic pH or to a specific enzyme. This was considered to be a particularly important feature of the conjugates, enabling them to be stable whilst in the blood stream or other extracellular environments, and allowing hydrolysis and the release of the selected agent only inside the target cells.

In designing an acid-labile bond, it is reasoned that the endocytosis of the conjugate by the endothelial cell would result in its delivery to acidified endosomes and lysosomes. This is known to occur with heparin itself (Fabian et al., 1978; Bârzu et al., 1985). The presence of the acid-labile bond would then allow the release of the selected agent from such acid intracellular compartments. The selected agents, such as steroids, would then be free to exert their effects only when inside the target cells, and would be otherwise maintained in an active state whilst circulating in the body.

A variety of acid-labile bonds could be employed to join the targeting component of a conjugate to the selected agent. For example, the inventor chose to utilize hydrazide linkers of the formulae:

or

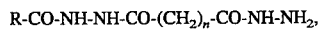

wherein n=1–4.

The use of hydrazide linkers in conjugates is believed to provide certain advantages. For example, related heparin-steroid conjugates with linkers of different length, i.e. with differing numbers of $CH_2$ groups, could be prepared using the same synthetic protocol. This may influence the rate of conjugate hydrolysis and allow one to engineer conjugates with different rates of release from the intracellular compartments, allowing a degree of control over the concentrations of active steroids in the cell.

Further acid-labile bonds that could be employed in accordance with the present invention incorporate ortho ester, acetal and ketal functionalities that undergo acid-catalyzed dissociation but are base-stable; and cis-aconitic, maleic, or citraconic acid functionalities having a free carboxyl group juxtaposed to the acid-sensitive amide or ester linkage.

In other instances, it is proposed that conjugates with an enzyme-sensitive bond such as an ester, a peptide, an amide, a phosphodiester or a glycoside will provide certain advantages. As this class of conjugates would be hydrolysed only by exposure to the specific enzyme, i.e. to an esterase, peptidase, an amidase, a phosphodiesterase or a glycosidase, this may allow conjugates to be engineered that are hydrolysed only at the endothelial cell surface, or within the precise intracellular compartments where the specific enzymes are located.

One major finding that has emerged from the inventor's studies clearly demonstrates that a particular conjugate, a heparin-cortisol inhibitor, had all the properties that were desired by the inventor. Namely, it inhibited DNA synthesis and migration of vascular endothelial cells in vitro, it retarded the vascularization of sponges implanted into mice, and it significantly inhibited the growth of solid Lewis lung carcinomas in mice. In each assay, the activity of the heparin-cortisol conjugate exceeded that of a mixture of its components showing that, as reasoned beforehand, chemical linkage of the components improved the biological activity of the conjugate.

The heparin-cortisol conjugate was constructed by first condensing the carboxyl groups of accessible glucuronic acid and iduronic acid residues in heparin with adipic dihydrazide. This resulted in the introduction of hydrazide groups into heparin which, on mixing with cortisol, condensed with the ketone group on C3 of the steroid to form a conjugate in which the heparin and the steroid were joined by an acyl hydrazone bond. This bond was stable at pH 7.4 but, as required, allowed the rapid dissociation of the conjugate at pH 4.8. The first destination of the conjugate following internalization would be the acidified endosomes and lysosomes, which, with a pH of ~4.8, would promote the rapid release of the steroid.

Derivatization of heparin to obtain the hydrazide destroyed the anticoagulant activity of heparin. This is consistent with earlier reports concerning the synthesis of heparinylglycine and heparinylglycine methyl ester (Danishefsky & Siskovic, 1971). The inventor proposes that modification of either or both of the two iduronic acid residues in the pentasaccharide sequence near to the non-reducing terminus (Lindahl et al., 1983) distorted its anti-thrombin binding activity. Importantly, the synthetic procedure left the sulfate groups, which are important for tight endothelial cell binding, unaltered.

Heparin-cortisol inhibited DNA synthesis in cultured proliferating vascular endothelial cells at lower concentrations than did a mixture of its components. In addition, it delayed the repair of wounded HUVE monolayers, suggesting that, in addition to inhibiting cell proliferation, it inhibited endothelial cell migration. These two effects may explain why total abolition of vascularization was observed in sponges injected with heparin-cortisol. Vascularization is a complex process requiring both the migration of vascular endothelial cells into the sponge and then proliferation to enable the capillary sprout to elongate. Administration of unconjugated mixtures of heparin and cortisol, or heparin hydrazide and cortisol, did not affect vascularization of sponges.

The injection of heparin-cortisol into mice bearing solid Lewis lung carcinomas also resulted in statistically significant anti-tumor effects. Heparin-cortisol-treated mice showed a reduction in tumor mass of approximately 65% relative to that in untreated controls, and of approximately 40% relative to that in recipients of unconjugated heparin hydrazide and cortisol.

The inventor proposes that these promising results may be improved upon further. It is possible that the inhibitory effects of systemically administered conjugates on tumor growth and sponge vascularization might be strengthened by a different dose regimen designed to increase and sustain blood levels. Since the effects of steroids on cell activation/proliferation are known to reverse rapidly when the steroid is removed, it is possible that a wave of endothelial cell proliferation occurred towards the end of each 24 hour interval between injections. If so, the problem should be solved simply by a continuous infusion of the conjugate. This can be investigated in animal models by employing an implanted mini-pump. If continuous infusion is found to be particularly advantageous in experimental animals, the inventor contemplates that biodegradable polymer-based drug-release capsules may be used clinically to allow the continuous supply of a conjugate.

As this invention provides a universally applicable means of targeting any drug or other component to a vascular endothelial cell, it is envisioned that novel conjugates of the present invention will find broad utility both in vivo and in vitro. Important medical uses range from anti-tumor therapy and the treatment of diabetic retinopathy, to the control of inflammatory responses. It is envisioned that a wide variety of conjugates could be synthesized, using different targeting polymers and selected agents, for use in the numerous clinical applications discussed above.

Conjugates of the present invention are also contemplated to be of use in research, for example, in investigating events such as the targeting, binding and uptake of polyanionic polymers, or in analyzing the specific effects of various components, including steroids, on endothelial cells. This includes analyzing the proliferation and migration of endothelial cells in experimental animals treated with certain conjugates, and also, investigating the in vivo expression, and particularly, the cell surface expression, of various molecules induced by such treatment.

The novel conjugates of the present invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a conjugate of the present invention and the pharmaceutically acceptable carriers are then easily administered in a variety of dosage forms such as injectable solutions, slow-release biodegradable capsules, and the like.

For parenteral administration, solutions of the conjugates in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Derivatization of Heparin

1. Materials

Heparin (sodium salt; H3125; Grade 1 from porcine intestinal mucosa, 181 USP units/mg), adipic dihydrazide, cortisol (hydrocortisone; 11β, 17α, 21-trihydroxypregna-4-ene-3, 20-dione; H4001) and Russell's viper venom (RVCL-1, freeze-dried powder reconstituted to 3 ml with saline) were from Sigma Chemical Co., St. Louis, Mo. Carbazole, sodium tetraborate, EDC (1-ethyl-3-(3-dimethylaminopropyl)-carbodiimide) and other chemicals were from Aldrich Chemical Co., Milwaukee, Wis. All reagents were Analar or equivalent, or the best grade available.

Goat anti-human Von Willebrand factor (vWF) antibody was purchased from DAKO Ltd., High Wycombe, England. $^3$H-thymidine and $^{133}$Xe were from Amersham International, Amersham, U.K. Polyether-polyurethane sponge (VP45) was a gift from Mr. M. Robinson, Vitafoam Ltd., Ashton-under-Lyne, U.K. Disks of diameter 0.8 cm were cut from sheets of the sponge using a cork-borer. Tissue culture medium (M199 with Earle's salts) was obtained from Gibco-Biocult Ltd., Paisley, Scotland. Fetal calf serum was obtained from ICN Biomedials, Inc., Costa Mesa, Calif. Endothelial cell growth supplement (0.12 mg/ml) was obtained from Sigma Chemical Co. Ninety-six well flat-bottomed microtiter plates and 24-well tissue culture plates were obtained from Falcon (Becton Dickinson & Co., Lincoln Park, N.J.).

2. Measurement of Heparin Concentration

The concentration of heparin solutions was determined by using a modification of the carbazole assay described by Bitter & Muir (1962). Briefly, the heparin solutions to be analyzed were diluted until their approximate concentration was in the range of 25–250 μg/ml. 200 μl of the heparin solutions were added dropwise to glass tubes containing 1 ml of an ice-cold solution of sodium tetraborate (5.03 mg/ml) in concentrated sulfuric acid. The solutions were mixed and heated at 95° C. for 10 minutes. 40 μl of carbazole (1.25 mg/ml) in absolute ethanol was added to each tube and the solutions were mixed and heated at 95° C. for 15 minutes. The tubes were allowed to cool and the optical density was measured at 530 nm. The heparin concentrations were calculated by comparing the optical densities of duplicate samples of the test solutions with those of standards prepared from heparin solutions having concentrations ranging from 0 to 250 μg/ml.

3. Condensation of Heparin and Hydrazine

Hydrazine (1,567 ml) was made up to 50 ml with 1M HCl, adjusted to pH 4.75 with 1M NaOH, and diluted to 100 ml. 20 ml of this solution was added to 200 mg of heparin, which dissolved on shaking. EDC in water (4 ml) was added to the hydrazine-heparin solution (20 ml) to give a EDC concentration of 10.7 mg/ml. The solution was adjusted at intervals to pH 4.75, dialyzed twice in 1 mM HCl and once in 0.05M borate solution with NaCl (1.7% w/v), and then three times in distilled water and was freeze dried.

4. Condensation of Heparin and Succinic Dihydrazide

A solution of heparin (100 mg/ml) in distilled water was filtered through a column of sepharose S200 (5×60 cm) to remove low molecular weight heparin present in this material. The fractions containing the highest molecular weight components were pooled until 70% of the heparin applied to the column had been recovered, and the lower molecular weight fractions were discarded. Heparin was then condensed with succinic dihydrazide in a similar manner to that described for the synthesis of heparinylglycine (Danishefsky & Siskovic, 1971). The concentrate was adjusted to 10 mg/ml and adipic dihydrazide was added to a final concentration of 0.5M. The pH of the solution was adjusted to 4.75 using 1M HCl. A freshly prepared solution of EDC in water was added to give a final EDC concentration of 10.7 mg/ml.

The reaction was allowed to proceed at room temperature while maintaining the pH at 4.75 (±0.02) by the periodic addition of 1M HCl. When the pH had stabilized (2–3 hours), the mixture was kept at 4° C. for 48 hours and was then dialyzed (using tubing having a $M_r$ cut-off of 3500) into 1 mM HCl in water at 4° C. with four changes of dialysis buffer over 4 days. The retentate was then freeze dried.

5. Condensation of Heparin and Adipic Dihydrazide

Low molecular weight heparin was removed from a solution of heparin (10 mg/ml) in distilled water by passing through an Amicon ultrafiltration cell fitted with a YM30 membrane until 30% of the heparin appeared in the filtrate. Heparin was then condensed with adipic dihydrazide in a similar manner to that described for the synthesis of heparinylglycine (Danishefsky & Siskovic, 1971). The concentrate was adjusted to 10 mg/ml and adipic dihydrazide was added to a final concentration of 0.5M. The pH of the solution was adjusted to 4.75 using 1M HCl. A freshly prepared solution of EDC in water was added to give a final EDC concentration of 10.7 mg/ml.

The reaction was allowed to proceed at room temperature whilst maintaining the pH at 4.75 (±0.02) by the periodic addition of 1M HCl. When the pH had stabilized (2–3 hours), the mixture was kept at 4° C. for 48 hours and was then dialyzed (using tubing have a $M_r$ cut-off of 3500) into 1 mM HCl in water at 4° C. with four changes of dialysis buffer over 4 days. The dialyzed solution was again extensively dialyzed into deionized water at room temperature. The resulting aqueous solution was freezedried and was stored in desiccator at 4° C.

EXAMPLE II

Conjugation of Heparin Derivatives

1. Conjugation of Daunomycin and Carminomycin to the Adipic Hydrazide Derivative of Heparin Daunomycin and carminomycin contain amino sugars which interact electrostatically with heparin and cause a precipitate to form. To avoid this, the amino group was first converted to the cis-aconityl derivative which is removed at acidic pH (i.e., at the same time as the conjugated drug dissociates from the heparin carrier).

Daunomycin or carminomycin (20 mg) were dissolved in 4 ml of 0.05M sodium borate buffer, pH 9, and stored on ice. To this solution were dropwise added 200 µl of a freshly-prepared solution of cis-aconitic anhydride (30 mg/ml) in dry dioxan. The reaction was allowed to proceed for 10 minutes on ice and then for a further 10 minutes at room temperature. Thin layer chromatography on silican plates run in 3:1 ethanol:H$_2$O revealed that >90% of the daunomycin and carminomycin had been converted to their cis-aconityl derivatives having Rf values of 0.75 as compared with 0.05 for the unreacted drugs. The acid lability of the introduced cis-aconityl protecting group was confirmed by mixing the cis-aconityl carminomycin with an equal volume of 1M sodium acetate buffer, pH 4.3. Samples were run on silica TLC plates in MeOH. The half life of dissociation of the derivatives back to native drugs was approximately 60 minutes under these conditions.

Next, the cis-aconityl daunomycin and cis-aconityl carminomycin were conjugated to the adipic hydrazide derivative of heparin via the .CO.CH$_3$ group present in the drugs. Heparin adipic hydrazide (46.1 mg) was dissolved in 3 ml of 0.5M sodium acetate buffer, pH 6.0. To this solution was added 0.68 ml of a 9 mM solution of cis-aconityl drug in dry dioxan. The solutions were mixed and allowed to react for 24 hours at room temperature. The solutions were then applied to columns of Sephadex G25 equilibrated in H$_2$O whose pH had been raised to 9 with dilute NaOH. The void volume peak was collected and freeze dried. Spectrophotometric (u.v) quantitation of the coupled drugs together with measurements of heparin concentration by carbazole assay gave the drug:heparin ratios as 1.6 mol:mol for daunomycin and 0.6:1 for carminomycin.

To confirm that the drugs could be released from the heparin adipic hydrazide carrier at acidic pH, an experiment was performed in which samples of heparin-daunomycin conjugate were incubated at pH 4.3 or pH 3.3 for various periods of time. The samples were then analyzed using a TLC system in which silica plates were run in 3:1 H$_2$O:MeOH. In this system, the conjugate moves with an $R_f$ of 0.6 whereas free daunomycin remains on the origin. Incubation of the conjugate at pH 3.3 at room temperature for 30 minutes caused complete dissociation of the conjugate to give free drug. By contrast, at pH 4.3, dissociation was slow: only about 10–20% of the conjugate dissociated within 4 hours. At pH 7, dissociation was undetectable. The daunomycin and carminomycin conjugates (Table III) have the structures shown in FIG. 1.

2. Conjugation of Mithramycin to the Adipic Hydrazide Derivative of Heparin

Figure 2:
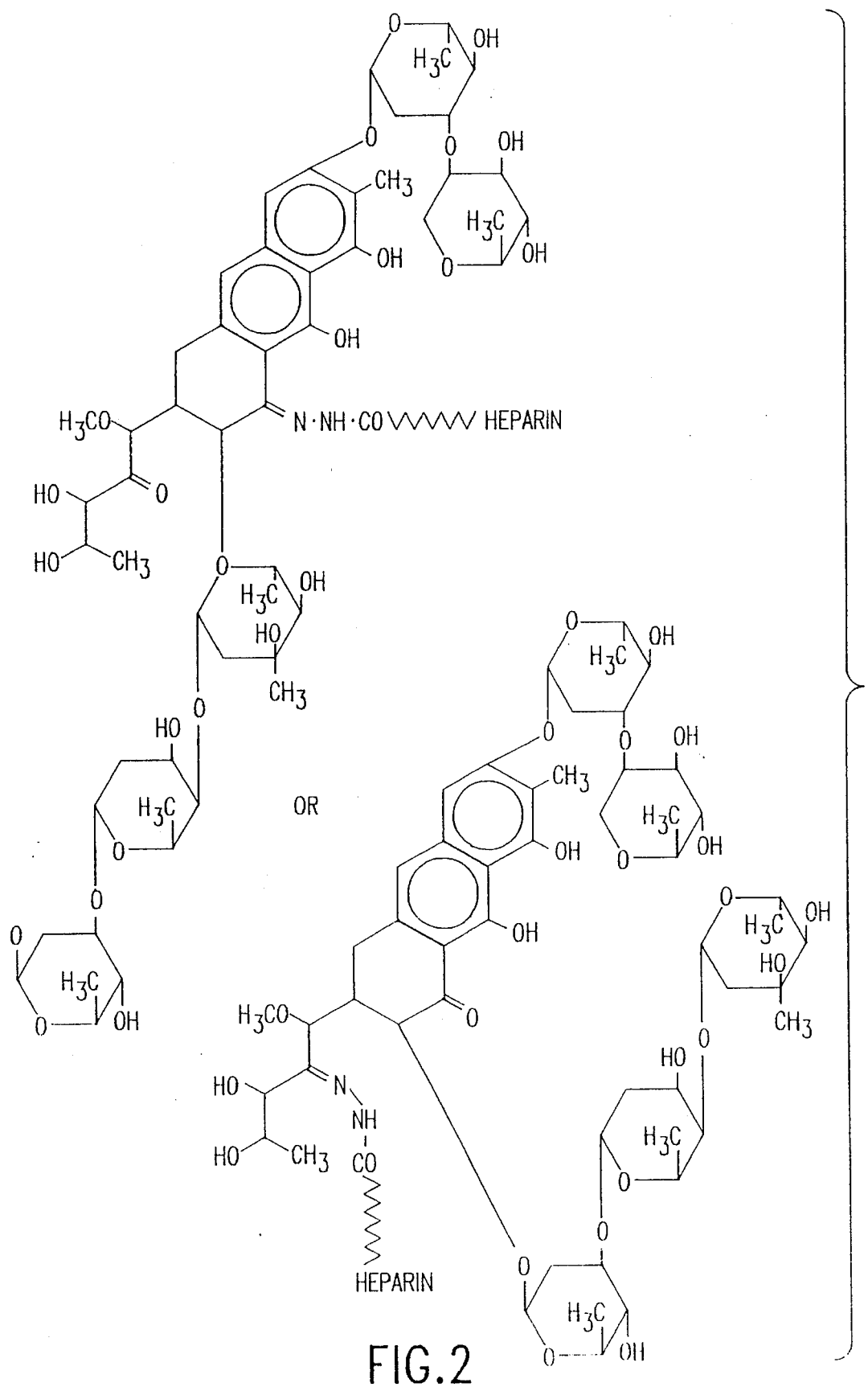
FIG. 2. Structure of heparin-mithramycin conjugates.

Heparin adipic hydrazide (70 mg) was dissolved in 6 ml of 0.1M sodium phosphate buffer, pH 5.8. Mithramycin (10 mg) was dissolved in 1 ml dimethylformamide and this solution was mixed with the heparin adipic hydrazide solution and left for 2½% days at room temperature. The reaction mixture was then applied to a column of Sephadex G25 equilibrated in H$_2$O whose pH had been raised to approximately 10 by the addition of dilute NaOH. The conjugate, which elated in the void volume, was collected and freeze dried. Quantitation of the drug by u.v spectrophotometric analysis and of the heparin by carbazole assay gave the composition of the conjugate as 0.54 mol mithromycin:mol heparin. The conjugate (Table III) has the structure shown in FIG. 2.

3. Conjugation of Aminopterin to the Adipic Hydrazide Derivative of Heparin

Direct Conjugation: Aminopterin (102 mg) was dissolved in 10 ml dimethyl formamide with gentle heating. To this solution was added 26.7 mg of N-hydroxysuccinimide dissolved in 0.315 ml dimethyl formamide, followed by 47.8 mg of dicyclohexylcarbodiimide dissolved in 0.523 ml of dimethylformamide. The mixture was allowed to react for 20 hours at room temperature. The urea that formed during the reaction was removed by centrifugation. Analysis by TLC on silica plates run in 1:1 methanol:H$_2$O showed that the product(s) ran with an $R_f$ of 0.85 as compared with 0.96 for aminopterin and 0.93 for N-hydroxysuccinimide.

To 27.3 ml of a 18.3 mg/ml solution of heparin adipic hydrazide in acetate buffer, pH 6.0, were added 6 ml of a 16 mM solution of the N-hydroxysuccinimide derivative of aminopterin in dimethylformamide. The reaction was allowed to proceed for 24 hours at room temperature. The mixture was then applied to a column of Sephadex G25 equilibrated in $H_2O$. The conjugate, which eluted in the void volume, was collected and freeze dried. Quantitation of the aminopterin content by u.v spectrophotometric measurements and of the heparin content by carbazole assay showed that the conjugate contained 1.66 mol aminopterin:mol heparin.

Figure 3:
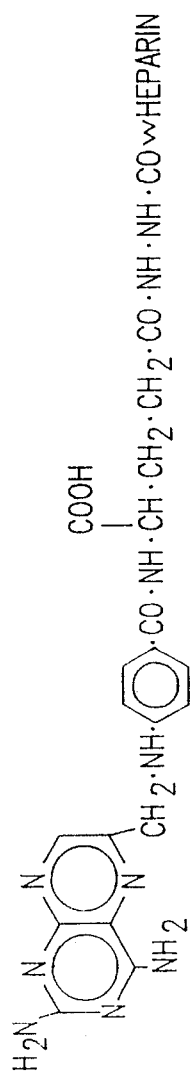
FIG. 3. Predominant structure of directly-linked heparin-aminopterin conjugate.

The conjugate (Table III) predominantly has the structure shown in FIG. 3 in which the aminopterin is linked through its γ COOH group to the heparin derivative.

Conjugation Via Leu-Ala-Leu-Ala Spacer: The N-hydroxysuccinimide ester of aminopterin was prepared as above. To 10.2 ml of a 23 mM solution of the aminopterin derivative (0,236 mmol) in dimethylformamide were added 104 mg (0,236 mmol) of solid L-Leu-L-Ala-L-Leu-L-Ala (LALA). The mixture was stirred overnight at 50° C. during which time the solid LALA dissolved. To the reaction mixture was added 48.7 mg (0.236 mmol) of dicyclohexylcarbodiimide in 0.58 ml of dimethylformamide. Copious quantities of urea formed within 2 hours at room temperature and were removed by filtration. The filtrate containing the N-hydroxy succinimide ester of the LALA derivative of aminopterin was retained.

To 500 mg of heparin adipic hydrazide at 19.3 mg/ml in 0.1M sodium acetate buffer, pH 6.0, were added 7.4 ml of a 13.5 mM solution of the N-hydroxysuccinimide ester of LALA-aminopterin in dimethylformamide. The reaction was left for 24 hours at room temperature in the dark. The reaction mixture was applied to a column of sephadex G25 equilibrated in $H_2O$. The conjugate, which eluted in the void volume, was collected. Quantitation of aminopterin content by u.v spectrophotometric measurements and of heparin content by carbazole assay showed that the conjugate contained 4.9 mol aminopterin:mol heparin.

Figure 4:
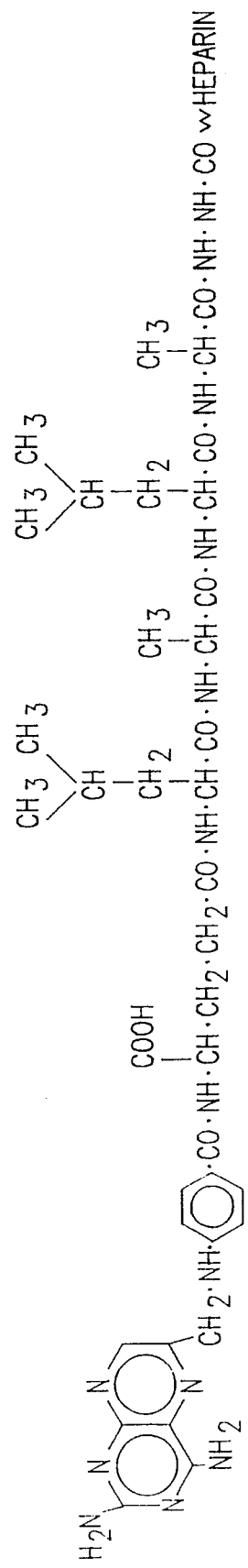
FIG. 4. Predominant structure of aminopterin-LALA-heparin conjugate.

The conjugate probably contained different species depending on which carboxyl group was esterified with N-hydroxysuccinimide at each stage of the reaction. However, the predominant reaction is with the most reactive and accessible carboxyl group. Thus, the conjugate (Table III) should predominantly have the structure shown in FIG. 4.

4. Further Heparin Conjugates

Heparin derivatives have also been conjugated to other selected agents, including 3-(2-pyridyldithio) propionic acid (PDP), biotin and ricin A chain, as represented below:

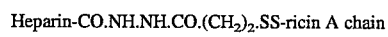

The PDP derivative was prepared by treating 5 ml of a solution of heparin adipic hydrazide (5 mg/ml) in 0.05M sodium borate butter, pH 9, with 0.2 ml of a solution of N-hydroxysuccinimidyl 3-(2-pyridyldithio)propionate (SPDP, Pharmacia Ltd.) (5.2 mg/ml) dissolved in dry dimethylformamide. The reaction was allowed to proceed for one hour at room temperature and the heparin derivative was then dialyzed into water. Quantitation of the introduced dithiopyridyl groups by the method of Carlsson et al. (Biochem. J. 173, 723, 1978) and of the heparin by carbazole assay gave the molar ratio of dithiopyridyl groups:heparin as 1.2:1.

The biotin derivative of heparin adipic hydrazide was prepared by treating 1 ml of a solution of heparin adipic hydrazide (5 mg/ml) in 0.05M sodium borate buffer, pH 9, with 0.2 ml of a solution of N-hydroxysuccinimidyl biotin amidocaproate (3.8 mg/ml) dissolved in dry dimethylformamide. The reaction was allowed to proceed for one hour at room temperature and the heparin-biotin conjugate was then dialyzed into water.

Ricin A-chain was conjugated to heparin adipic hydrazide by mixing 5 ml of a 1 mg/ml solution of PDP-heparin (prepared as above) with 10 mg of freshly-reduced ricin A-chain in phosphate-buffered saline, pH 7.4. The thiol-disulfide exchange reaction leading to conjugation was allowed to proceed for 24 hours. The conjugate was fractionated on a column (2.2×80 cm) of Sephadex G75 and the leading edge of the major protein band which eluted was collected. Polyacrylamide gel electrophoresis in sodium dodecyl sulfate (SDS/PAGE) showed that the conjugate mainly (70%) consisted of a component approximately 50 kDa corresponding to one molecule of heparin coupled to one molecule of ricin A-chain.

5. Conjugation of Different Steroids to Heparin Adipic Hydrazide

TABLE III

CONJUGATES OF HEPARIN AND CHEMOTHERAPEUTIC DRUGS

| DRUG | LINKAGE | HEPARIN DERIVATIVE | MECHANISM OF HYDROLYSIS |
|---|---|---|---|
| *Daunomycin | Acyl hydrazone | Adipic hydrazide | acid-catalyzed |
| *Carminomycin | Acyl hydrazone | Adipic hydrazide | acid-catalyzed |
| Mithramycin | Acyl hydrazone | Adipic hydrazide | Acid-catalyzed |
| Aminopterin | Amide | Adipic hydrazide | Amidase |
| Aminopterin | Leu—Ala—Leu—Ala | Adipic hydrazide | Peptidase |

*as cis-aconityl derivatives

A solution of heparin adipic hydrazide (1.0 mg/ml) in 0.025M sodium acetate buffer pH 3.0 was prepared. A solution of the steroid in ethanol was added to give a final molar excess of steroid over hydrazide groups of 10-fold, and a final ethanol concentration of 30% (v/v). The steroid and the heparin adipic hydrazide were allowed to react at different temperatures and for different periods of time depending on the reactivity of the ketone groups of the steroid. The reaction conditions were:

a) 48 hours at room temperature;

b) 72 hours at room temperature with stirring;

c) 7 days at room temperature;

d) 10 days at 56° C.

The reaction conditions employed for the synthesis of conjugates with different steroids are listed in Table IV.

After the reaction, the pH of the mixture was adjusted to pH 10 with 10M NaOH. The heparin-steroid solution was then dialyzed extensively against water whose pH had been adjusted to 10 with a few drops of 1M NaOH. The heparin-steroid conjugate was finally freeze dried and stored in a desiccator at 4° C.

6. Conjugation of Different Steroids to the Hydrazine and Succinic Dihydrazide Derivatives of Heparin (Method (e))

The condensation products of heparin and hydrazine on succinic dihyrazide were dissolved in 0.5M sodium acetate buffer pH 4.0 at 4.9 mg/ml. Aqueous solutions or suspensions of steroids were added in 10–20 fold molar excess over hydrazide groups and the mixture stirred for 24 hours at room temperature. The mixture was then adjusted to pH 9 with 10M NaOH. The conjugate was separated from unconjugated steroid by gel filtration on a column of sepharose G25 equilibrated in water whose pH had been adjusted to 10 with 1M NaOH. The fractions containing the conjugate were pooled and freeze dried.

TABLE IV

EXAMPLES OF HEPARIN-STEROID CONJUGATES

| STEROID | HEPARIN DERIVATIZATION | LINKAGE METHOD |
|---|---|---|
| Cortisol | Adipic dihydrazide | (a) |
| 17α-hydroxyprogesterone | Adipic dihydrazide | (a) |
| Cortisone | Adipic dihydrazide | (a) |
| Corticosterone | Adipic dihydrazide | (a) |
| Deoxycorticosterone | Adipic dihydrazide | (a) |
| Progesterone | Adipic dihydrazide | (a) |
| Testosterone | Adipic dihydrazide | (a) |
| Pregnenolone | Adipic dihydrazide | (a) |
| Cortexolone | Adipic dihydrazide | (b) |
| Estrone | Adipic dihydrazide | (b) |
| Tetrahydrocortisone | Adipic dihydrazide | (c) |
| Tetrahydrocorticosterone | Adipic dihydrazide | (c) |
| Tetrahydrocortisol | Adipic dihydrazide | (d) |
| Tetrahydro S | Adipic dihydrazide | (d) |
| Dexamethasone | Adipic dihydrazide | (d) |
| Cortisol | Hydrazine | (e) |
| Cortisol 21-phosphate | Hydrazine | (e) |
| Cortisol 21-hemisuccinate | Hydrazine | (e) |
| Dexamethasone | Hydrazine | (e) |
| Dexamethasone 21-phosphate | Hydrazine | (e) |
| Dexamethasone 21-phosphate | Succinic dihydrazide | (e) |

EXAMPLE III

Structure and Properties of Heparin-Cortisol Conjugates

This example relates largely to the structure and chemical properties of the conjugate formed between cortisol and heparin adipic hydrazide.

1. Preparation

Heparin, from which the low molecular weight species had been removed, was condensed with adipic dihydrazide in a similar manner to that employed in the synthesis of heparinylglycine (Danishefsky & Siskovic, 1971), as described above in Example I, Section 5. The heparin adipic hydrazide was then dialyzed into 0.1M sodium acetate buffer, pH 4.0 and this solution adjusted to 1 mg/ml by addition of 0.1M sodium acetate buffer, pH 4.0.

The conjugation reaction was performed as outlined in Example II, Section 5. A solution of cortisol (11 mg/ml) in ethanol was added to the heparin-hydrazide solution to give a final cortisol concentration of 3.2 mg/ml and a final ethanol concentration of 30% (v/v). The mixture was allowed to react for 16 hours at room temperature and was then adjusted to pH 10 with 1M NaOH. The resultant heparin-cortisol was dialyzed extensively into water whose pH had been adjusted to 10 with a few drops of 1M NaOH. The dialyzed product was finally freeze-dried and stored in a desiccator at 4° C.

2. Structure

The molar ratio of cortisol to heparin in this product was determined by measuring the bound cortisol and heparin concentrations in a standard solution. The heparin concentration was determined using the carbazole method described above and the molar concentration was calculated assuming an average molecular weight of 15,000 Da (Bârzu et al., 1986). The cortisol concentration was measured spectrophotometrically at 274 nm, using an extinction coefficient of 21,900 $M^{-1}$ for the acyl hydrazone derivative of cortisol. This extinction coefficient was determined by dissociating samples of heparin-cortisol at acidic pH and measuring the released cortisol concentration from the optical density at 242 nm (using the extinction coefficient of 16,100 $M^{-1}$ (Budavari, 1989) after correcting for 242 nm absorbance due to the heparin-hydrazide. The molar ratio of cortisol:heparin in the product was usually found to be between 8 and 9.

Figure 5:
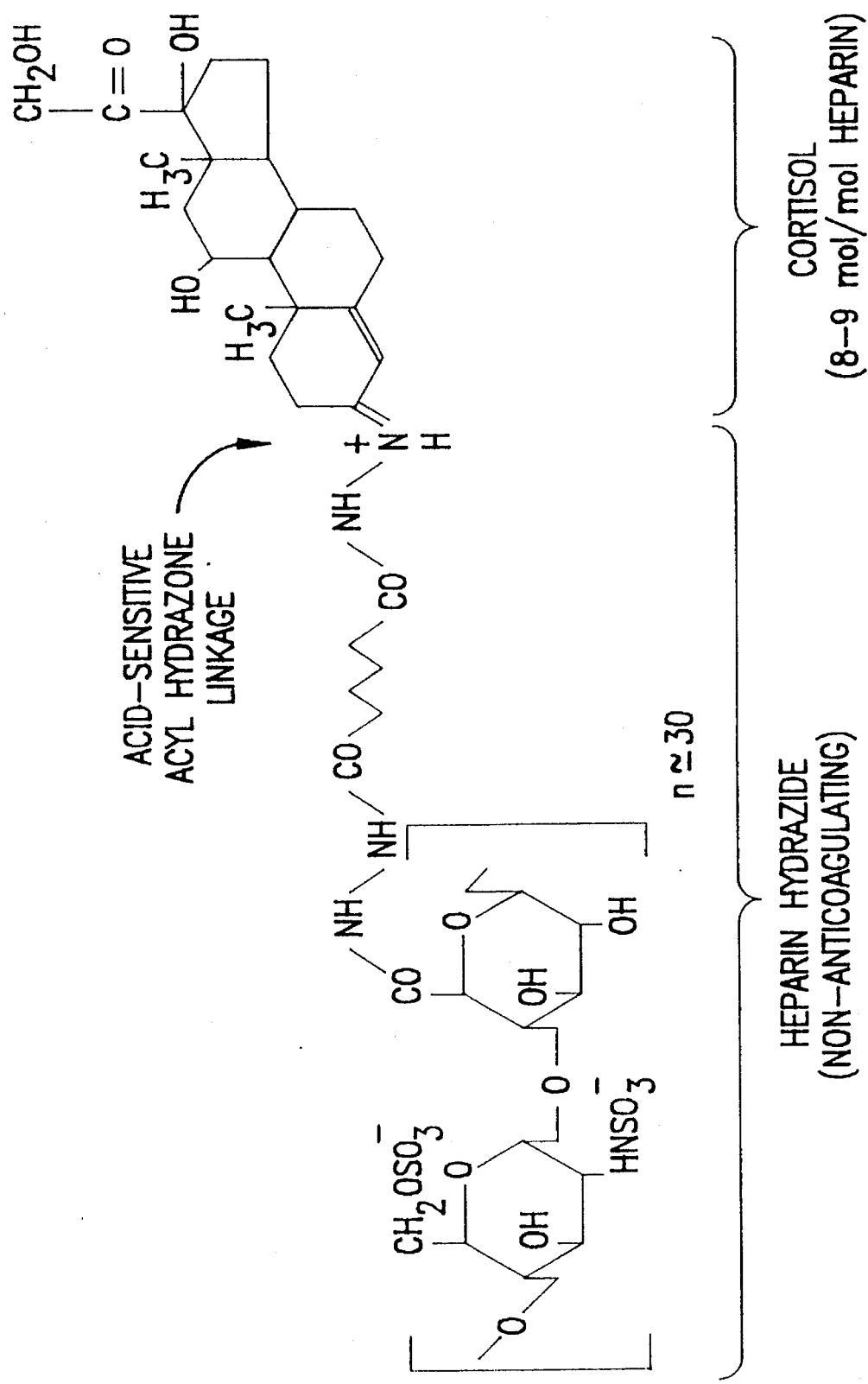
FIG. 5. Structure of heparin-adipic hydrazide-cortisol conjugate.

The structure of this heparin-cortisol product is schematically represented in FIG. 5. There are two ketones in cortisol which could have potentially reacted with the hydrazide, one at C3 on the A-ring and the other at C20 on the side chain. However, significant reaction only appears to have occurred with the C3 ketone, under the conditions used in the present study, to give the product depicted in FIG. 5. This is evident from the fact that the chromophoric A-ring of cortisol, which has a UV spectrum having a $\lambda_{max}$ at 242 nm, changes on reaction with hydrazides to a product having a $\lambda_{max}$ at 274 nm: a change in the absorption properties of the A-ring would not be expected if the linkage were with the C20 ketone.

3. Acid Lability 0.75 ml of a solution of a heparin-cortisol conjugate (200 µg/ml) in distilled water was added to a 1.5 ml spectrophotometer cell in a thermostatically-controlled holder maintained at 20° C. or 37° C. For analysis at pH 4.8, 0.75 ml of 0.1M sodium acetate, pH 4.8, was added and the contents of the cell were rapidly mixed. The UV spectrum from 400 nm to 200 nm was scanned immediately and every 5 minutes thereafter until the decomposition of the heparin-cortisol was complete. The half-life of the decomposition was taken as the time for the OD at 274 nm to decay to half its initial value.

Figure 6:
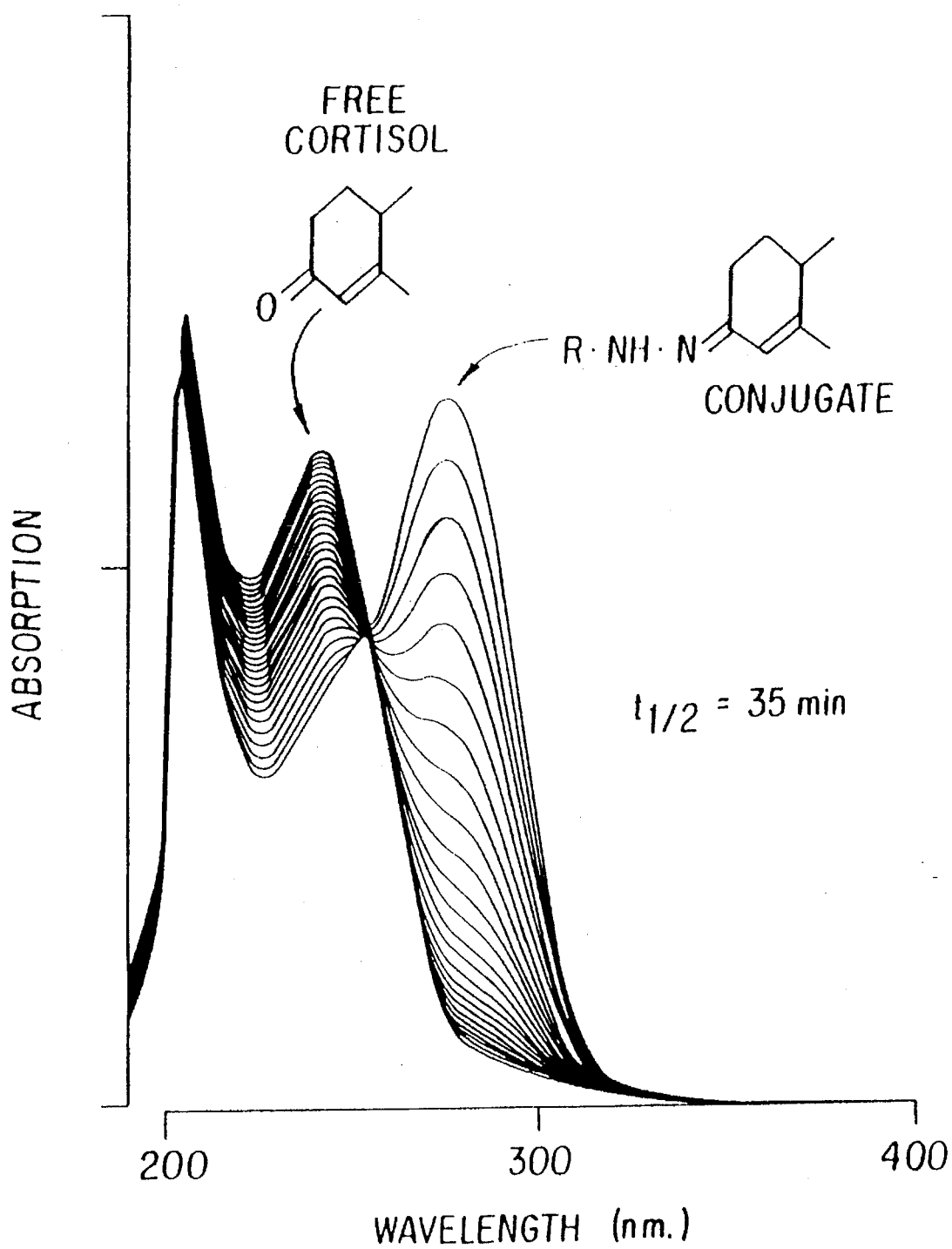
FIG. 6. Dissociation of heparin-adipic hydrazide-cortisol at pH 4.8. The u.v. spectrum of cortisol coupled via C3 to heparin adipic hydrazide has a maximum at 274 nm, whereas free cortisol has a maximum at 242 nm. When heparin-cortisol (120 μg/ml) is incubated at pH 4.8 it dissociates to give free cortisol with a half-life of 35 minutes at 20° C. and 15 minutes at 37° C.. The conjugate does not dissociate detectably at pH 7.4.
Figure 7A:
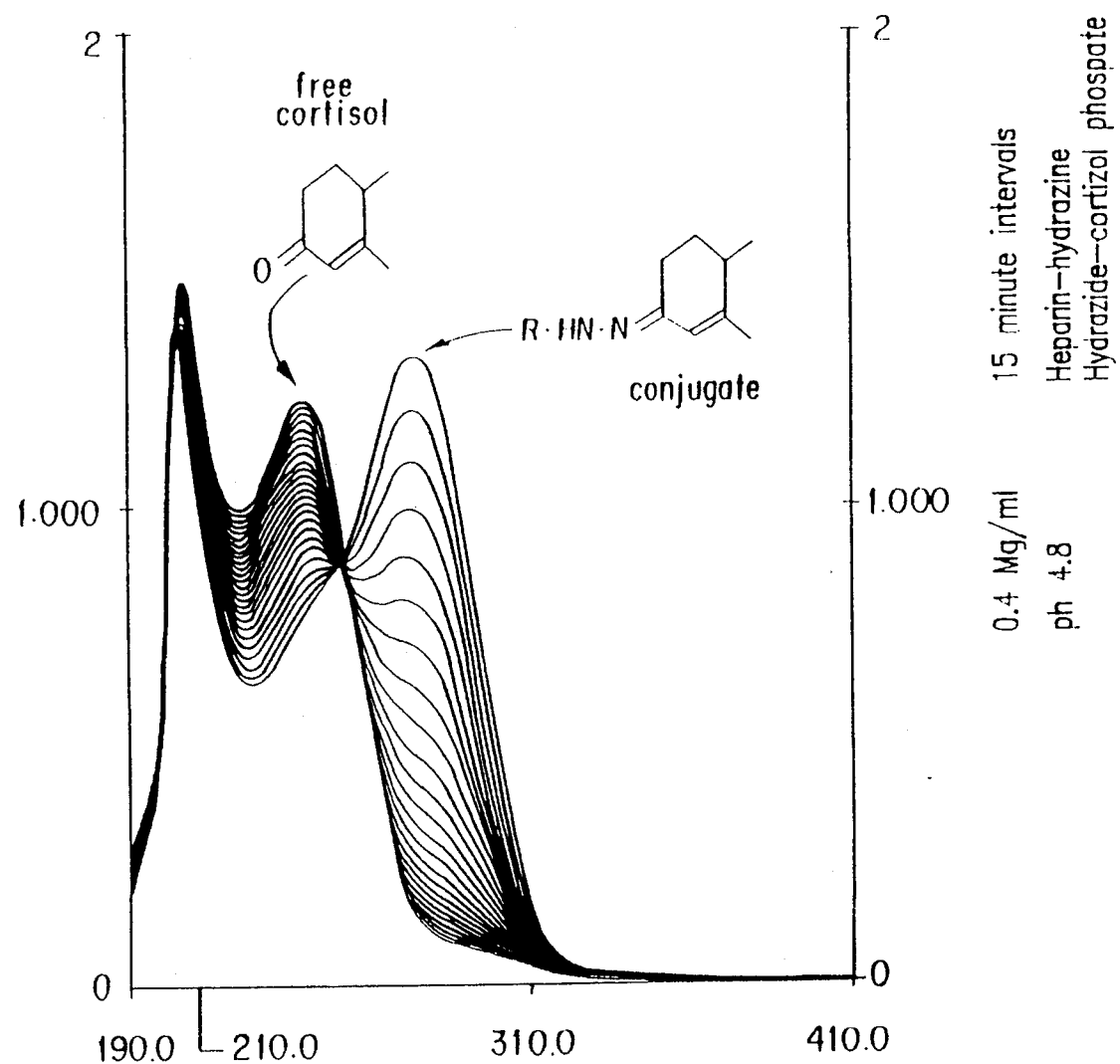
FIG. 7. Dissociation of heparin-hydrazine hydrazide-cortisol phosphate (A) and heparin-adipic hydrazide-cortisol phosphate (B) at pH 4.8.
Figure 7B:
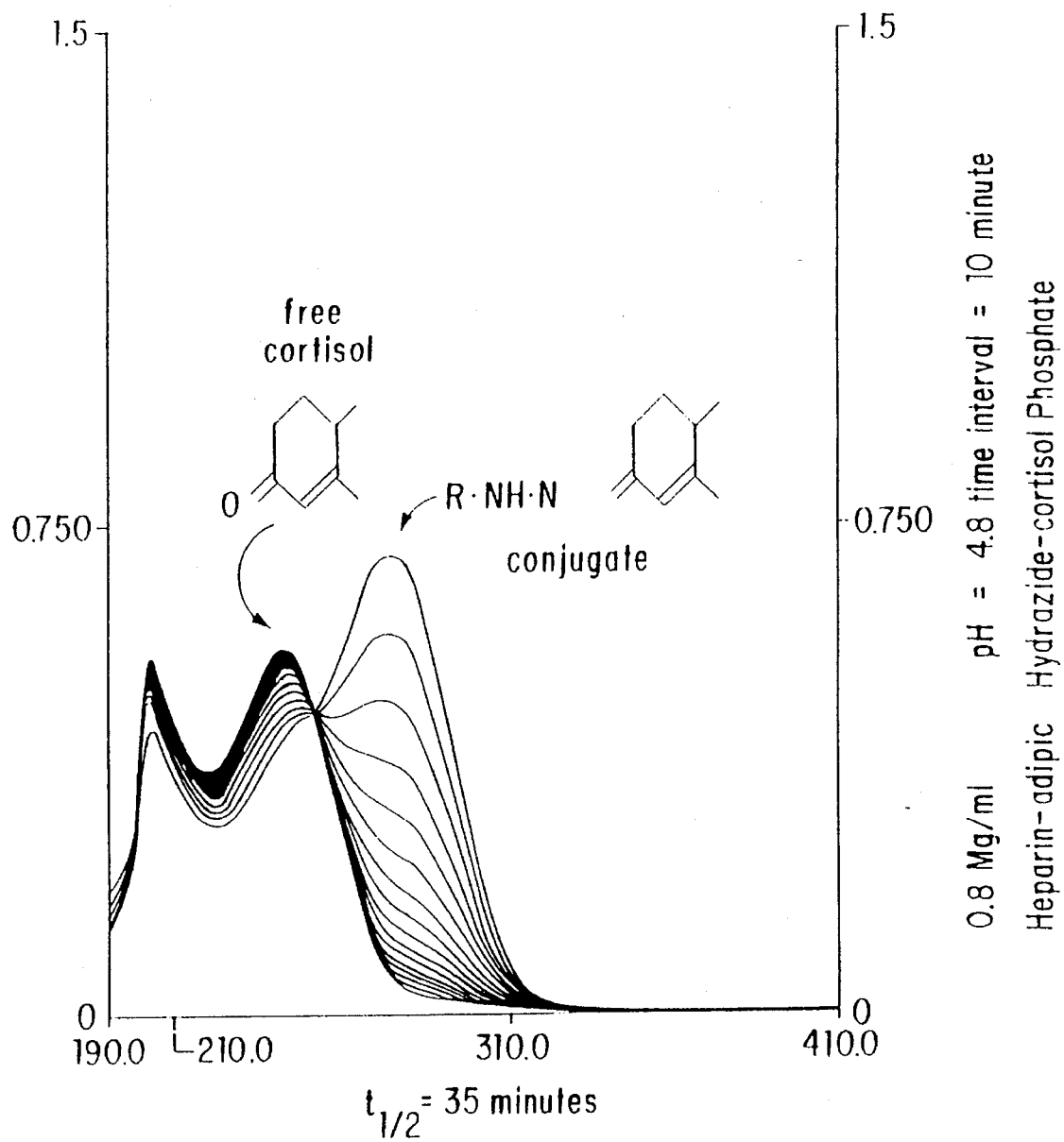

The dissociation of this heparin-cortisol conjugate is represented in FIG. 6, and the half-lives of dissociation shown in Table V. Data obtained for two heparin-cortisol phosphate conjugates are also presented (Table V, FIG. 7). At pH 7.4, the conjugate formed between cortisol and heparin adipic hydrazide was relatively stable: only 8% breakdown had occurred after 24 hours at 20°. However, this conjugate broke down to give free cortisol and heparin-hydrazide at pH 4.8, with a half-life of 35 minutes at 18° C. to 20° C., and 15 minutes at 37° C. (Table V, FIG. 6). Therefore, the acyl hydrazone bond joining the two components of the conjugate was markedly acid-labile, as expected. Uptake of heparin-cortisol by endothelial cells and delivery of the conjugate to acidified endosomes and lysosomes would thus be expected to lead to the rapid release of the steroid since these intracellular compartments have a pH of approximately 4.8.

4. Anticoagulant Activity

The anticoagulant activities of heparin, heparin-hydrazide, and the resultant heparin-cortisol conjugate were measured by their ability to inhibit coagulation of human plasma by Russell's viper venom. 20 µl solutions of heparin, heparin-hydrazide or heparin-cortisol at a range of concentrations from 1–1000 µg/ml in phosphate-buffered saline (PBS) were added to glass tubes which had been prewarmed to 37° C. Fresh citrated human plasma (150 µl) at 37° C. was added to each tube. The contents were immediately mixed and the tubes were incubated at 37° C. for 1 minute. One hundred microliters of Russell's viper venom (Sigma# RVCL-1 reconstituted to 3 ml) were added and the contents were mixed. After 15 seconds, 100 µl of a prewarmed solution of $CaCl_2$ (0.2M) in PBS were added. The contents of the tubes were immediately mixed and the tubes were incubated at 37° C. The time for the plasma to clot was recorded. The clotting times for plasma treated with heparin-hydrazide or heparin-cortisol were compared to those treated with unmodified heparin and the differences in anticoagulant activities were calculated.

TABLE V

| | HALF-LIVES OF DISSOCIATION OF HEPARIN-CORTISOL CONJUGATES AT pH 4.8 | | |
|---|---|---|---|
| STEROID | HEPARIN DERIVATIVE | TEMPERATURE | $T_{1/2}$ (minutes) |
| Cortisol | Adipic dihydrazide | 18° C. | 35 |
| Cortisol | Adipic dihydrazide | 37° C. | 15 |
| Cortisol phosphate | Adipic dihydrazide | 18° C. | 35 |
| Cortisol phosphate | Hydrazine | 18° C. | 90 |

Heparin hydrazide and the heparin-cortisol conjugate formed therefrom were found to be virtually devoid of anticoagulant activity, having less than 1% of the anticoagulant activity of native heparin, i.e. less than 2 USP units/mg. This destruction of anticoagulant activity on derivatization is in agreement with results reported by Danishefsky and Siskovic (1971) for heparinylglycine and heparinylglycine methyl ester. Presumably, modification of either or both of the two iduronic acid residues in the pentasaccharide sequence near to the non-reducing terminus (Lindahl et al., 1983) distorts its anti-thrombin binding activity. The absence of anti-coagulant activity of the product is advantageous because hemorrhage is unlikely to be a problem when heparin-cortisol is administered to animals. The heparin-cortisol should, however, retain its ability to bind to endothelial cells because the sulfate groups which are important for tight binding are unaltered.

EXAMPLE IV

In Vitro Inhibition of DNA Synthesis and Wound Repair by Heparin-Cortisol

This, and the following examples (V and VI), relate to the action of the conjugate formed between cortisol and heparin adipic hydrazide.

1. Methods a) DNA Synthesis by Human Endothelial Cells In Vitro

Human umbilical vein endothelial cells (HUVE) were isolated from fresh human umbilical cords as described by Jaffe et al., (1973). Cultures were maintained at 37° C. in an atmosphere of 5% $CO_2$ in humidified air in Medium 199 supplemented with Earle's salts, 20% (v/v) fetal calf serum (FCS), endothelial growth supplement (0.12 mg/ml), 0.09 mg/ml heparin, 2.4 mM L-glutamine, 200 units/ml penicillin and 100 µg/ml streptomycin. Cells were cultured in tissue culture flasks precoated with 1% (w/v) gelatin and were used at the third or fourth passage. Cultures were judged to by >95% endothelial cells by morphological criteria and by positive staining of monolayers with monoclonal anti-vWF antibody, F8/86 (Naieum et al., 1982).

Studies designed to determine inhibition of DNA synthesis were performed as follows: HUVE cells were removed from confluent tissue culture flasks with trypsin (0,025% w/v) and EDTA (ethylenediaminetetraacetic acid, 0.02% w/v). A cell suspension was prepared at $10^4$ cells/ml in culture medium containing all supplements with the exception of heparin. The suspension was distributed in 100 µl aliquots into the wells of 96-well flat bottomed microtiter plates which had precoated with 1% (w/v) gelatin in water. The cells were incubated for 24 hours at 37° C. during which time they adhered to and spread onto the surface of the wells. 100 µl solutions of heparin-cortisol or various control substances dissolved in heparin-free tissue culture medium were then added and the cells were incubated for 24 hours at 37° C. Each culture was then pulsed with 1µCi $^3$H-thymidine for 24 hours. The cells were washed with PBS, detached with trypsin-EDTA, and harvested onto glass fiber disks using an automated cell harvester. Acid insoluble radioactivity in treated cultures was expressed as a percentage of that in cultures treated with medium alone to obtain the % inhibition of DNA synthesis. All cultures were set up in triplicate.

b) DNA Synthesis by 3LL Cells In Vitro

Experiments designed to measure inhibition of DNA synthesis were performed in a manner similar to that described above for HUVE cells. 100 µl of a suspension of 3LL cells at $4 \times 10^4$ cells/ml in complete medium were distributed into 96-well microtiter plates, and incubated for 24 hours at 37° C. 100 µl of solutions of heparin-cortisol or various control substances were then added and cultures were incubated for 24 hours at 37° C., 1µCi/culture of $^3$H-thymidine was added and the quantity of label incorporated into TCA-insoluble material was determined.

c) Repair of Wounded HUVE Monolayers

The culture medium above confluent HUVE cultures (in 24-well tissue culture plates) was exchanged for medium containing all supplements except heparin. The cells were cultured for 2 days and were then wounded with a plastic micropipet tip (Eppendorf). The wounds were approximately 0.5 mm wide and 5–7 mm long. To the wounded monolayer cultures was added heparin-cortisol at a final concentration of $10^{-5}$M with respectto heparin ($1.4 \times 10^{-4}$M with respect to cortisol). Other wounded cultures were treated with heparin-hydrazide ($10^{-5}$M) alone, cortisol alone ($1.4\times10^{-4}$M), or with an unconjugated mixture of both. The cultures were incubated at 37° C. for 5 days and were photographed.

2. Results and Discussion a) Inhibition of DNA Synthesis of HUVE Cells

Figure 8A:
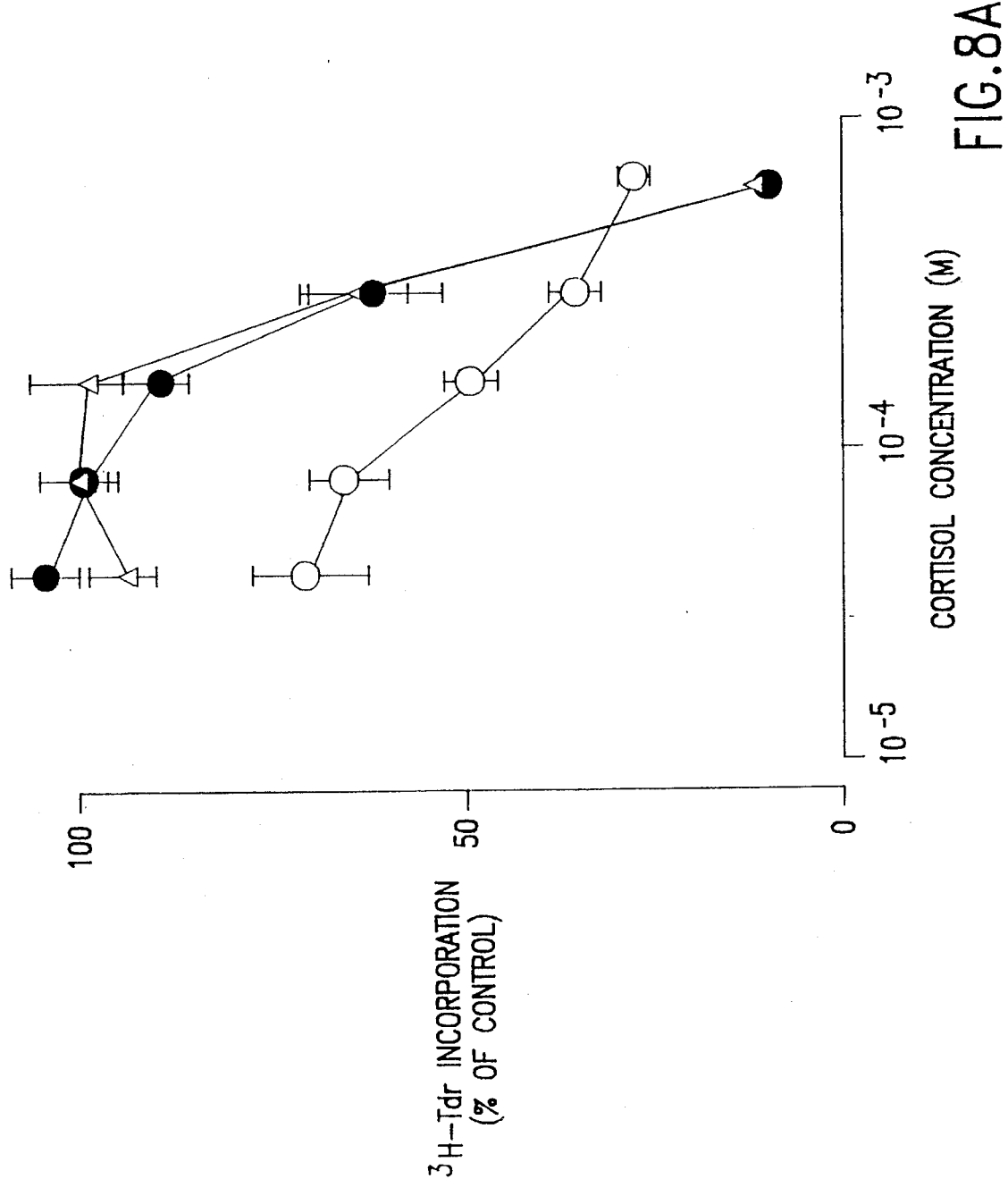
FIG. 8. Inhibition of DNA synthesis of HUVE cells by heparinadipic hydrazide-cortisol. HUVE cells were allowed to adhere to gelatin-coated microplate wells for 24 hours and were then treated for 24 hours at 37° C. with heparin-cortisol (○), with an equivalent mixture of unconjugated heparin hydrazide and cortisol (●), or with cortisol alone (▲). Concentrations in the figure refer to the cortisol concentration in each treatment. The capacity of the cells to incorporate $^3$H-Tdr into DNA was determined 24 hours later. $^3$H-Tdr incorporation is expressed as a percentage of that in untreated control cultures.
Figure 8B:
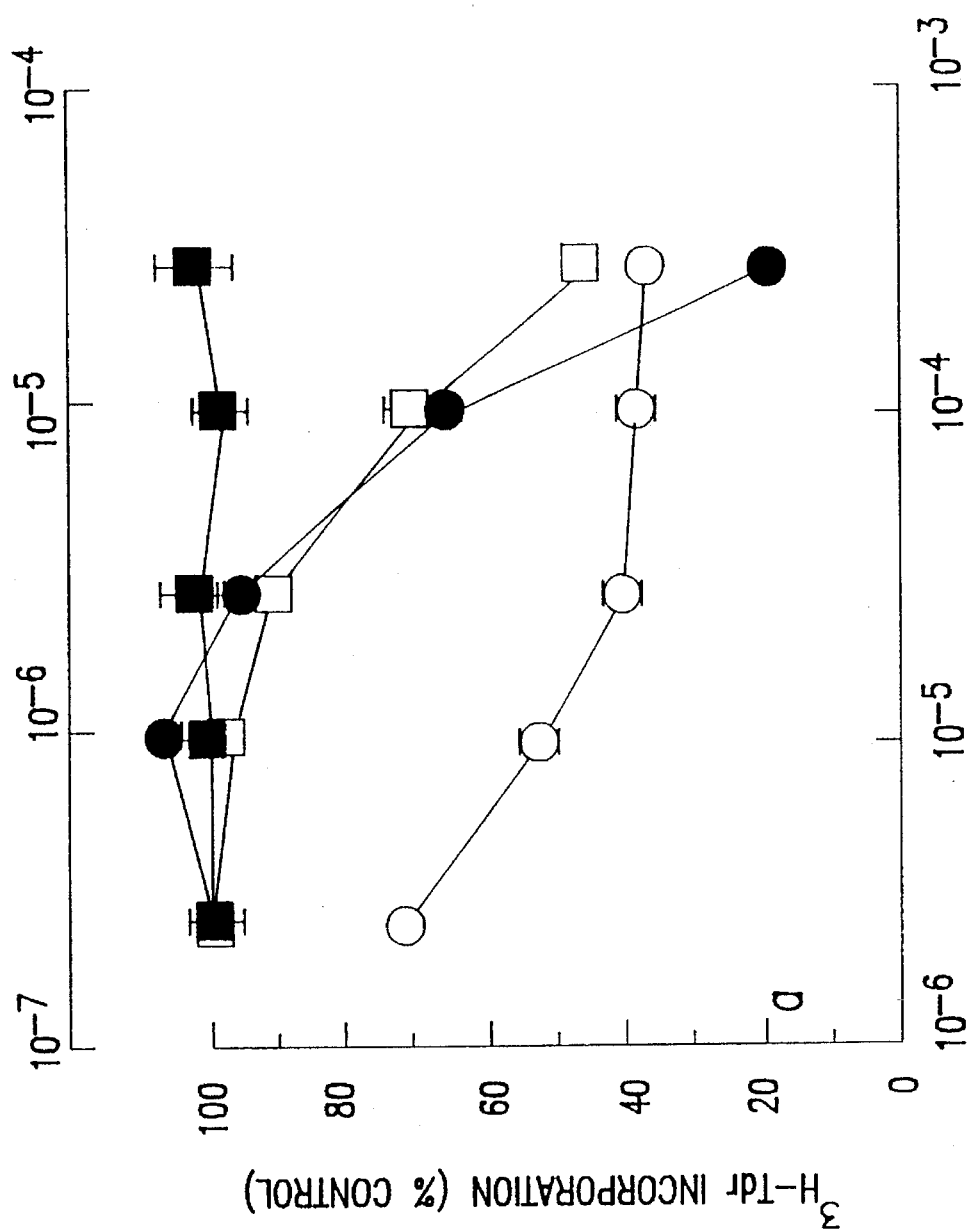
Figure 8C:
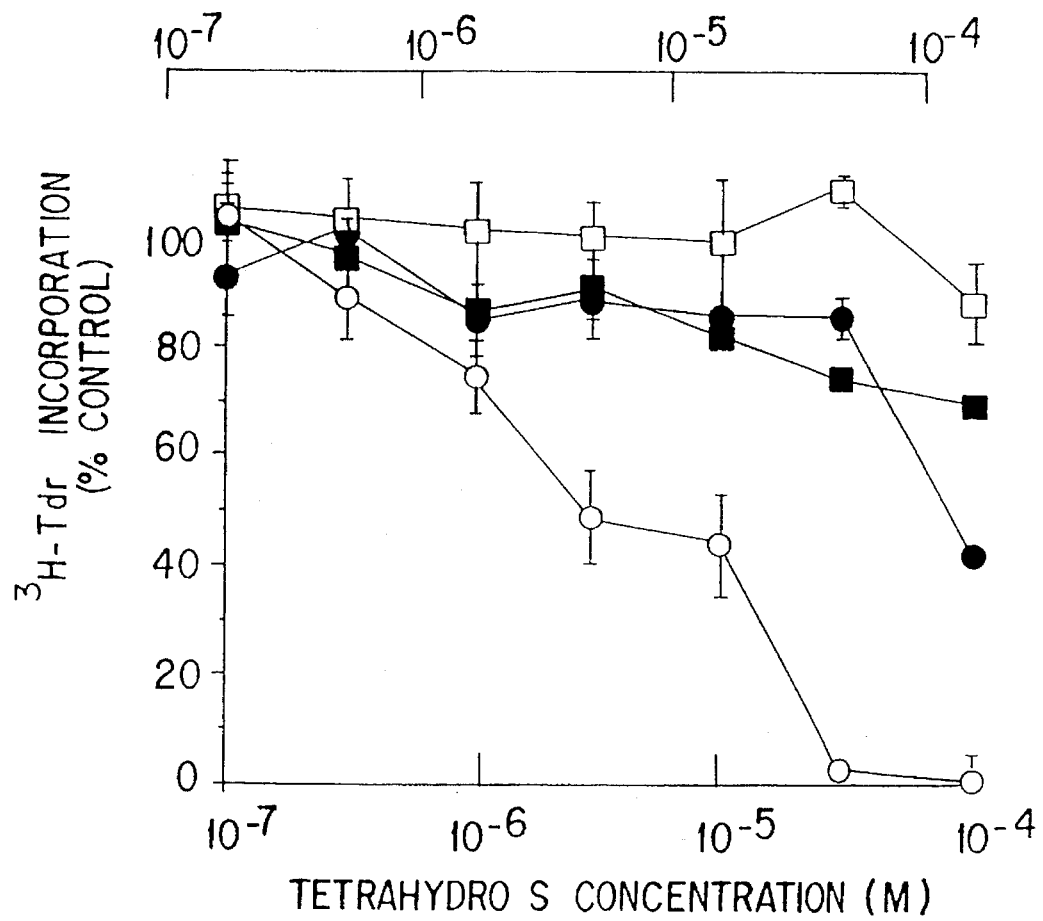

At concentrations below $4\times10^{-4}$M with respect to cortisol, heparin-cortisol inhibited DNA synthesis by HUVE cells to a significantly greater extent than did free cortisol or an unconjugated mixture of heparin hydrazide plus cortisol (FIG. 8). At $1.6\times10^{-4}$M with respect to cortisol ($2\times10^{-5}$M with respect to heparin-hydrazide), the conjugate inhibited DNA synthesis by 50%, whereas, at this same concentration, neither free cortisol nor the heparin-hydrazide plus cortisol mixture were inhibitory. However, at higher concentrations, the inhibitory effect of free cortisol surpassed that of the heparin-cortisol conjugate. At $6\times10^{-4}$M with respect to cortisol, the inhibitory effect of heparin-cortisol reached a maximum of 70%, whereas at the same concentration, free cortisol inhibited DNA synthesis by 90%. This suggests that the uptake pathway for heparin-cortisol had become saturated at this concentration whereas that for cortisol had not. Heparin hydrazide was not inhibitory over the concentration range shown in FIG. 8.

To confirm that the heparin-cortisol conjugate was binding to heparin receptors on HUVE cells, the experiment was repeated with the inclusion of competing levels of free native heparin ($10^{-3}$) in the cultures. The presence of the competing ligand abolished the inhibitory effect of heparin-cortisol showing that, as expected, the effects of the conjugate were mediated through binding to heparin receptors.

b) Inhibition of DNA Synthesis in 3LL Cells

In contrast with HUVE cells, Lewis lung carcinoma (3LL) cells were relatively insensitive to heparin-cortisol. Treatment of 3LL cells with heparin-cortisol at $10^{-3}$M with respect to cortisol reduced their DNA synthesis by only 36%. This same level of inhibition of HUVE cells was obtained with a 40-fold lower concentration of heparin-cortisol. Heparin-cortisol was also less inhibitory than was free cortisol or cortisol mixed with heparin hydrazide, which again contrasted with HUVE cells. When applied at $10^{-3}$M with respect to cortisol, these agents inhibited DNA synthesis by 65 and 69% respectively. Thus, uptake of cortisol by 3LL cells is hindered rather than facilitated by its attachment to heparin, presumably because these cells lack receptors to bind the heparin moiety.

c) Inhibition of Repair of Wounded HUVE Monolayers

Heparin-cortisol retarded the repair of wounded HUVE cell monolayers. In wounded monolayers treated with free cortisol ($1.6\times10^{-4}$M) or with an unconjugated mixture of heparin-hydrazide plus cortisol ($1.6\times10^{-4}$M), migration of HUVE cells into the wounded area began within 24 hours and was complete by 72 hours. By contrast, in wounded monolayers treated with heparin-cortisol at $1.6\times10^{-4}$M with respect to cortisol, little wound repair was evident by 5 days. This indicates that, in addition to inhibiting DNA synthesis, heparin-cortisol inhibits the migration of HUVE cells. Importantly, the cells in the unwounded areas of the culture remained morphologically healthy showing that heparin-cortisol inhibited migration and proliferation but was not toxic to quiescent cells.

EXAMPLE V

Anti-Angiogenic Effects of Heparin-Cortisol In Vivo

1. Methods a) Vascularization of Implanted Sponges

Measurements of the extent of vascularization of sponge implants in mice were made using the method of Andrade et al., (1987) with slight modifications. Sterile polyether-polyurethane sponge disks (0.8 cm diameter×0.4 cm thickness) were prepared which contained a 1.2 cm length of polypropylene tubing (1.4 mm external diameter) protruding from the center of one circular face of the sponge and located 0.2 cm deep into the sponge (i.e., midway through its thickness). The cannula was sewn into the sponge with silk sutures and its open end was sealed with a removable plastic plug. Male BALB/c mice aged 8–12 weeks were anesthetized and the sponges were aseptically implanted into a subcutaneous pouch which had been fashioned with curved artery forceps through a 1cm long dorsal midline incision. The cannula was exteriorized through a small incision in the subcutaneous pouch.

Vascularization of the sponge was assessed twice weekly after implantation by anesthetizing the mice and injecting 10 μl of a sterile solution of $^{133}$Xe in saline ($5\times10^5$ dpm/ml) into the sponge via the cannula. The cannula was immediately plugged to prevent escape of the gas. A collimated gamma scintillation detector was then situated 1cm above the sponge and the radioactivity was measured for 5 seconds each minute for 9 minutes. The radioactivity-versus-time data were fitted to an exponential decline curve using a least-squares regression algorithm and the half-life of clearance was computed. In freshly implanted avascular sponges the $^{133}$Xe was cleared slowly with a half-life of about 25 minutes whereas in a fully vascularized sponge the $^{133}$Xe was cleared rapidly with a half-life of about 7 minutes. Normally, full vascularization of an implanted sponge occurred in about 16 days.

Two types of experiments were performed in which the effect of heparin-cortisol on vascularization of sponges was determined. In the first, heparin-cortisol (0.78 mg) in 25 μl saline was injected into the sponge via the cannula every day for 10 days starting the third day after implantation. Other groups of mice received equivalent quantities of heparin-hydrazide (0.65 mg), cortisol (0.13 mg) or an unconjugated mixture of both. In the second series of studies, mice received intraperitoneal injections of heparin-cortisol (2.35 mg) or heparin-hydrazide (1.95 mg) plus cortisol (0.39 mg) in 0.25 ml saline every day for 5 days starting on the third day after implantation, and then half these doses for the next 7 days. Each treatment group contained 10 mice. Effects on vascularization were judged from changes in $^{133}$Xe clearance rate. Differences in clearance rates were tested for statistical significance using Willcoxin's log-rank test (Swinscow, 1980).

b) Enumeration of Blood Vessels and Endothelial Cells in Implanted Sponges

An experiment was performed in which heparin-cortisol (1 mg) was injected daily into implanted sponges via the cannula for 10 days starting 3 days after implantation. Other mice received equivalent doses of heparin hydrazide (0.83 mg), cortisol (0.17 mg), or of an unconjugated mixture of heparin hydrazide (0.83 mg) plus cortisol (0.17 mg). A further group received an unconjugated mixture of native heparin (0.83 mg) plus cortisol (0.17 mg). Sponges were dissected out and transverse frozen sections were cut from half way through the sponge's thickness. Endothelial cells and blood vessels were identified by indirect immunoperoxidase staining with goat anti-human vWF antibody which crossreacts with mouse vWF. Blood vessels were visible as vWF-positive structures with discernable lumens. About half of the vessels contained erythrocytes. Endothelial cells were visible as vWF-positive cells having the morphology of endothelial cells but lacking an adjacent lumen. The vessels and endothelial cells present in 15 microscope fields (in a diametric line across the section) were counted.

2. Results

Inhibition of Vascularization of Implanted Sponges

Daily injections of heparin-cortisol (0.78 mg) into implanted sponges in mice abolished vascularization of the sponge. This was evident from the fact that (i) the $^{133}$Xe clearance rate of the heparin-cortisol-treated sponges remained the same as that of freshly implanted (avascular) sponges for as long as the injections were continued (FIG. 9a), and (ii) frozen sections of sponges from mice that had received 10 daily injections of heparin-cortisol were completely devoid of endothelial cells or blood vessels, as identified by anti-vWF staining (Table VI).

Heparin-cortisol was the only substance which retarded the $^{133}$Xe clearance rates. In control groups which received equivalent quantities of heparin hydrazide alone, cortisol alone, or a mixture of the two, $^{133}$Xe clearance rates were the same as in mice which received saline alone (Table VI). However, the number of blood vessels and endothelial cells present in sections of sponges which had been injected with heparin hydrazide, either alone or mixed with cortisol, were reduced by about 45% and 65% respectively as compared with sponges injected with saline alone (Table VI). It is unclear why reductions in the number of blood vessels and endothelial cells in sponges injected with heparin hydrazide did not give rise to reductions in $^{133}$Xe clearance rate. Conceivably, $^{133}$Xe clearance rates are a fairly insensitive indicator of vascularization and major differences in vascularity are needed for perceptible differences in $^{133}$Xe clearance rates.

TABLE VI

ABOLITION OF VASCULARIZATION OF IMPLANTED SPONGES BY DAILY INJECTIONS OF HEPARIN-CORTISOL INTO THE SPONGE

| Material injected[a] | Number in 15 microscope fields[b] | |
|---|---|---|
| | Blood vessels[c] (with lumens) | Endothelial cells[c] (without lumens) |
| Saline | 61 ± 18 | 96 ± 22 |
| Heparin-cortisol conjugate | 0 | 0 |
| Heparin hydrazide | 34 ± 18 | 31 ± 14 |
| Cortisol | 47 ± 12 | 74 ± 10 |
| Heparin hydrazide plus cortisol | 33 ± 13 | 35 ± 6 |
| Native heparin plus cortisol | 52 (41–63) | 42 (35–48) |

[a]Doses were 1.0 mg heparin-cortisol, 0.83 mg heparin hydrazide, 0.17 mg cortisol, 0.83 mg heparin hydrazide plus 0.17 mg cortisol, or 0.83 mg native heparin plus 0.17 mg cortisol.
[b]Fifteen fields were counted which formed a straight line from the edges to the center of each sponge. The numbers given are the average number of vessels and endothelial cells in all 15 fields from sponges taken from 4 to 7 mice ± one standard deviation. In the case of native heparin plus cortisol, only 2 sponges were analyzed: the numbers in parentheses are the total number of vessels and endothelial cells of the 15 fields of the two sponges.
[c]Vessels and endothelial cells were identified by indirect immunoperoxidase staining with rabbit anti-vWF antibody.

In other systems, native heparin and glucocorticosteroids have synergistic anti-angiogenic activity (Crum et al., 1985; Folkman, 1985). We therefore determined the effect of injecting a mixture of native heparin and cortisol daily into implanted sponges on the vascularization of the sponge. The treatment neither retarded the $^{133}$Xe clearance rate nor reduced the number of blood vessels in the sponge (FIG. 9a and Table VI).

Figure 9B:
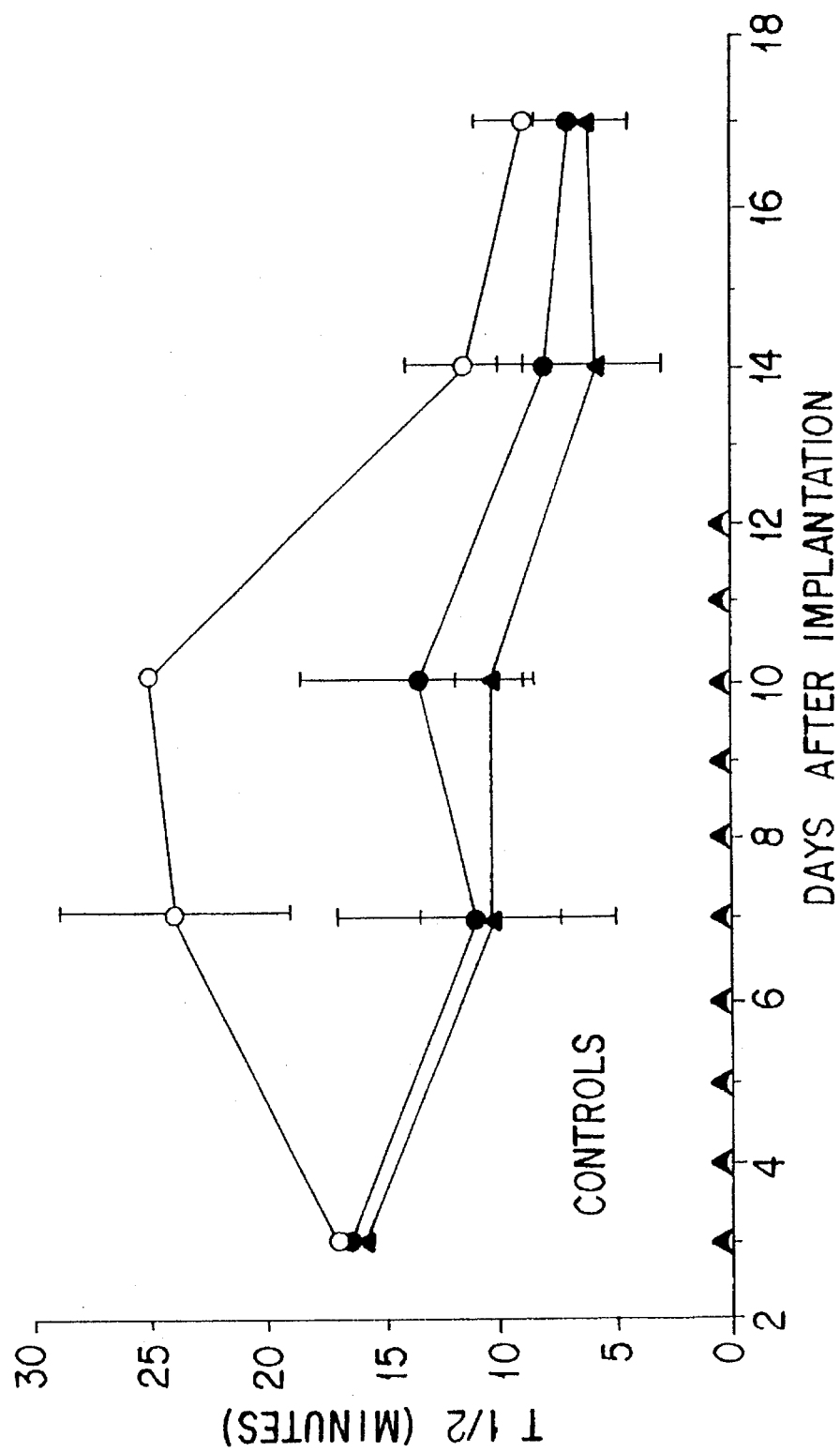
FIG. 9. Delayed vascularization of implanted sponges in mice by administration of heparin-adipic hydrazide-cortisol. Polyurethane sponges were implanted subcutaneously into mice. The extent of vascularization of the sponges was assessed at various times thereafter by injecting $^{133}$Xe into the sponges and measuring the rate of disappearance of radioactivity. As vascularization proceeds, the half-life of $^{133}$Xe clearance falls from about 25 minutes to about 7 minutes. In (a), starting 3 days after implantation, heparin-cortisol (0.78 mg) was injected daily for 10 days directly into the sponge (○). Other mice received equivalent quantities of a mixture of unconjugated heparin hydrazide (0.65 mg) plus cortisol (0.13 mg) (●), cortisol (0.13 mg) alone (■), unmodified heparin (0.33 mg) plus cortisol (0.13 mg) (Δ), or diluent (▲). In (b), starting 3 days after implantation, mice were injected intraperitoneally with 2.35 mg heparin-cortisol for 5 days and then with 1.17 mg heparin-cortisol for a further 7 days (○). Other mice received equivalent quantities of unconjugated heparin hydrazide plus cortisol (●), or diluent (▲). Each treatment group consisted of 10 mice.

A further experiment was performed in which mice were given daily intraperitoneal injections of high doses of heparin-cortisol (2.35 mg) for 5 days and then half this dose (1.17 mg) for 7 days. The dose was reduced during the experiment because the mice showed local bruising of the abdomen in the vicinity of the injection site. Measurements of $^{133}$Xe clearance rates showed that vascularization was significantly (P<0.05) retarded only while the larger doses were being given. Mice treated with equivalent amounts of a mixture of unconjugated heparin hydrazide and cortisol showed similar $^{133}$Xe clearance rates to those in recipients of saline alone (FIG. 9b).

The above data indicates that the conjugate-mediated inhibition of DNA synthesis and cell migration observed with cultured vascular endothelial cells also occurs in vivo. Vascularization is a complex process requiring both the migration of vascular endothelial cells into the sponge and then proliferation to enable the capillary sprout to elongate. Injection of heparin-cortisol into implanted sponges resulted in the total abolition of vascularization, whereas the administration of unconjugated mixtures of heparin and cortisol, or heparin hydrazide and cortisol, did not affect vascularization. This last result is in contrast to other reports (Crum et al., 1985; Folkman, 1985).

EXAMPLE VI

Anti-Tumor Effects of Heparin-Cortisol In Vivo

1. Methods

Male C57 BL/6 mice aged 8–12 weeks were injected subcutaneously with 3×10$^6$ Lewis lung carcinoma (3LL) cells which had been maintained in tissue culture. The tumor is an anaplastic epidermoid carcinoma which originated as a spontaneous lung tumor in a C57BL mouse in 1951 (Sugiura & Stock, 1955). When the tumors had grown to measurable dimensions (about 0.3 cm in diameter), the mice were injected intravenously with 0.1 ml of saline containing 1 mg heparin-cortisol every day for 9 days. Other mice received equivalent quantities of heparin-hydrazide (0.85 mg), cortisol (0.15 mg), or a mixture of both. On the tenth day, the mice were sacrificed and their tumors were removed and weighed. All treatment groups contained 8–10 mice. Differences in tumor weights were tested for statistical significance using Student's t-test.

2. Results and Discussion

Figure 10:
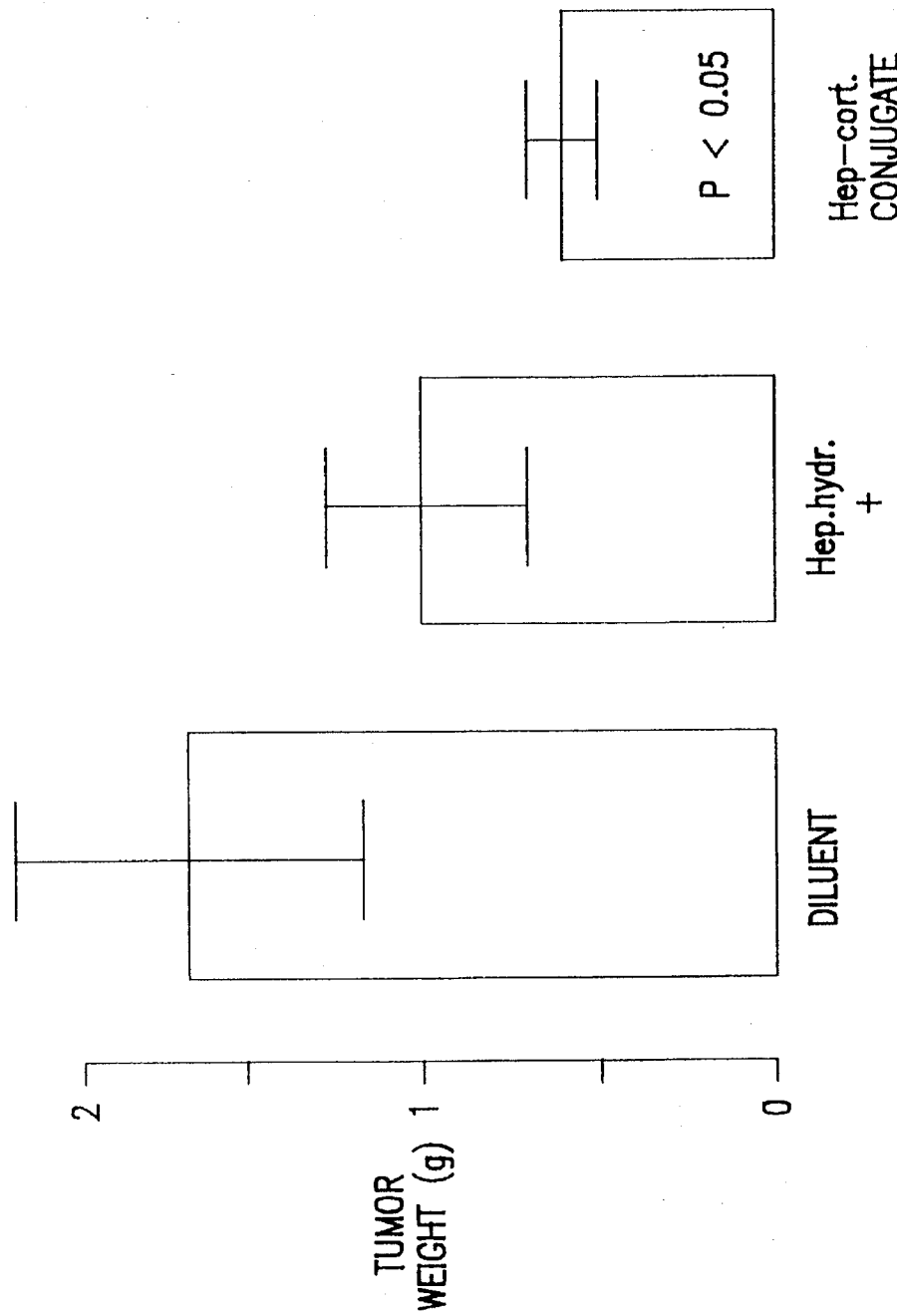
FIG. 10. Anti-tumor effects of heparin-adipic hydrazide-cortisol. Mice were injected subcutaneously with 3LL Lewis lung carcinoma cells. When the tumors reached approximately 0.3 cm in diameter, the mice were injected daily with the heparin-cortisol conjugate (1 mg) or with equivalent quantities of heparin hydrazide plus unconjugated cortisol or with diluent alone. Tumors were removed on day 10 after the onset of treatment and were weighed. The bars show the mean tumor weight per group ±one S.D.

Daily intravenous injections of heparin-cortisol (1 mg) into mice bearing established subcutaneous Lewis lung carcinomas reduced the average weight of the tumors to 35% of that in mice treated with saline alone and to 60% of that in mice treated with an unconjugated mixture of heparin hydrazide (0.85 mg) and cortisol (0.15 mg) (FIG. 10). These differences were statistically significant to the level of P<0.01 and P≦0.05, respectively. In mice receiving cortisol alone (0.15 mg/day), the average tumor weights were the same as in the group receiving both heparin hydrazide and cortisol. No reduction in tumor weight was observed in mice receiving heparin hydrazide alone (0.85 mg/day). Analogous results were obtained in two separate experiments.

In a further experiment, the treatment with heparin-cortisol was started three days before the 3LL cells were given and was continued for 10 days. The relative tumor weights were almost the same as those shown in FIG. 10. Hence, earlier treatment did not improve the anti-tumor effects of the heparin-cortisol.

Figure 11:
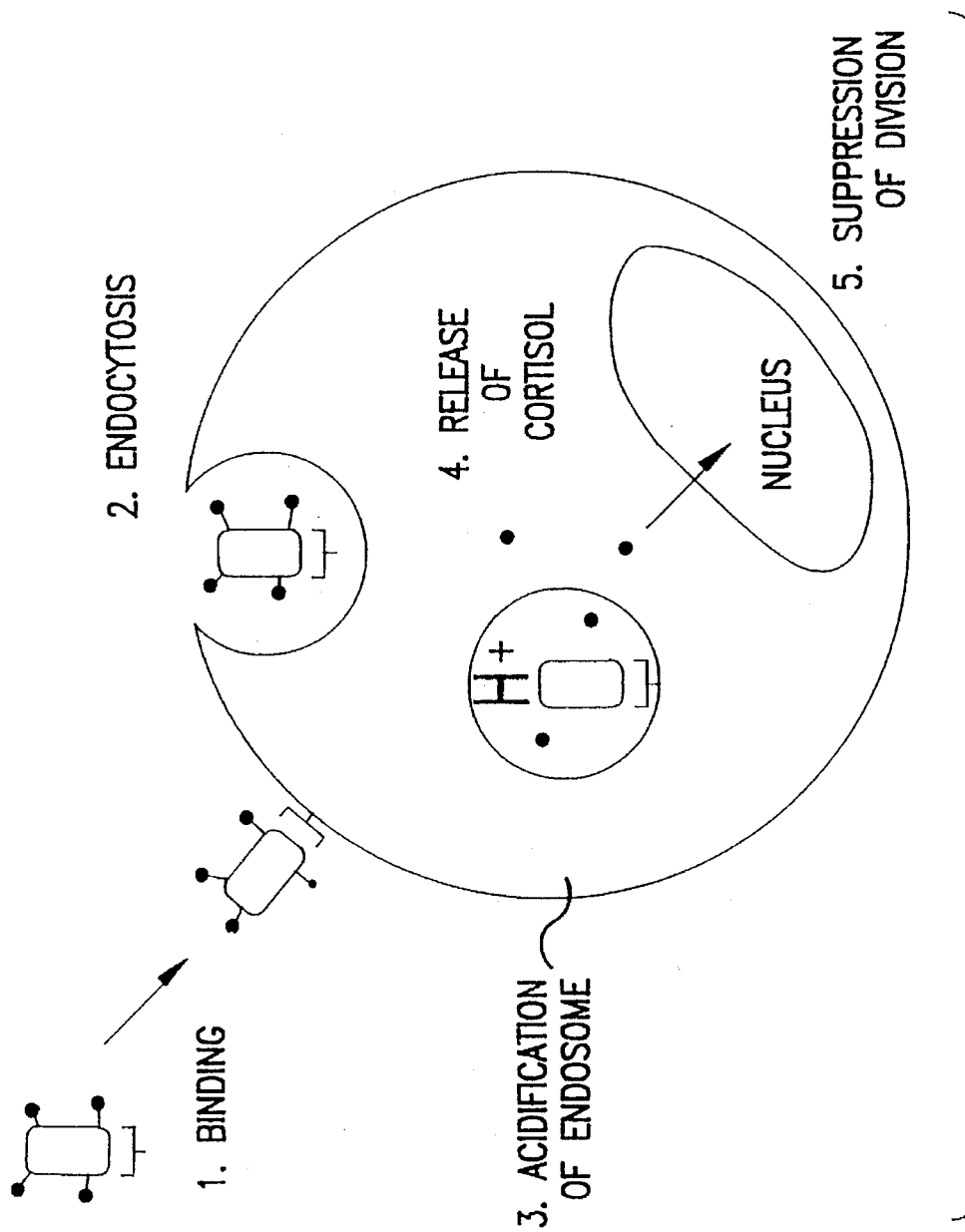
FIG. 11. Possible Mechanism of Action of Heparin-Cortisol.

The mechanism of action of heparin-cortisol is believed to be similar to that represented in FIG. 11. It is possible that the inhibitory effects of systemically administered heparin-cortisol on tumor growth and sponge vascularization might be improved by a different dose regimen designed to increase and sustain blood levels. Since the effects of steroids on cell activation and proliferation rapidly reverse when the steroid is removed (Folkman et al., 1973, 11690), it is possible that a wave of endothelial cell proliferation occurs towards the end of each 24 hour interval between injections. If so, the problem should be solved simply by a continuous infusion of the conjugate.

It is also possible that heparin-cortisol is rapidly removed by blood vessels in normal tissues following systemic administration, and that little drug reaches blood vessels in the tumor or sponge. However, this is highly unlikely. As the total number of vascular endothelial cells in the mouse is approximately $5 \times 10^8$ (Anggard, 1990) and the number or heparin receptors per endothelial cell is $10^6$ to $10^7$ (Bârzu et al., 1986), the entire vasculature of the mouse contains a total of $0.5-5 \times 10^{15}$ heparin receptors. A standard dose of heparin-cortisol (1 mg/injection) would supply approximately $5 \times 10^{16}$ heparin-cortisol molecules, which exceeds the total number of heparin of heparin receptors by 10 to 100-fold. Thus, saturation of heparin receptors on blood vessels in the tumor or sponge is predicted to occur after each administration of heparin-cortisol. Biodistribution studies are needed to confirm this prediction.

Despite compelling evidence to the contrary (Folkman, 1990), it is possible that solid tumors are not completely angiogenesis-dependent and that tumor growth can continue, even in the presence of an angiogenesis inhibitor, by infiltration of tumor cells along existing vascular tracts. This appears to be true of lymphomas (Denekamp & Hobson, 1982) and it is possible that the Lewis lung carcinoma used in the present study resembles lymphomas in this regard. Measuring the rate of endothelial cell division in tumors in mice on heparin-cortisol therapy will allow this point to be resolved.

The inventor proposes that angiostatic steroids (e.g. tetrahydro S) lacking glucocorticoid and mineralocorticoid activity (Crum et al., 1985) may be substituted for cortisol in the conjugate. These steroids appear to be ideal for coupling to heparin because they should give potent anti-angiogenic in animals without causing the toxic side effects normally associated with long term corticosteroid therapy. Long term treatment is likely to be needed in tumor therapy to suppress the outgrowth of dormant or anoxia-resistant tumor cells.

In conclusion therefore, the major findings to emerge in the present study are that heparin-cortisol inhibits DNA synthesis and migration of vascular endothelial cells in vitro, retards vascularization of sponges implanted into mice, and significantly inhibits the growth of solid Lewis lung carcinomas in mice. In each assay, the activity of the heparin-cortisol conjugate exceeded that of a mixture of its components showing that chemical linkage of the components improves the biological activity of the conjugate. The heparin-cortisol conjugate of the present invention thus represents the prototype of a new class of angiogenesis inhibitors with anti-tumor activity. By refining the choice of steroid and carrier moieties and the dose regimen for the administration of the conjugates the inventor proposes that the clinical usefulness of these drugs will be increased.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Algire, G. H., Chalkley, H. W., Legallais, F. Y., and Park, H. D. *J. Natl. Cancer Inst.*, 6:73–85, 1945.

Alpern-Elran, H., et al., *J. Neurosurg.* 70:942, 1989.

Andrade, S. P., Fan, T. P., and Lewis, G. P. *Br. J. Exp. Pathol.*, 68:755–766, 1987.

Anggard, E. E. *J. Endocrinolo*, 127:371–375, 1990.

Bârzu, T., Molho, P., Tobelem, G., Petitou, M., and Caen, J. *Biochim. Biophys. Acta*, 845:196–203, 1985.

Barzu, T., Van Rijn, J. L. M. L., Petitou, M., Molho, P., Tobelem, G., and Caen, J. P. *Biochem. J.*, 238:847–854, 1986.

Benrezzak, O., Madarnas, P., Pageau, R., Nigam, V. N., and Elhilali, M. M. *Anticancer Res.*, 9:1883–1888, 1989.

Bitter, T. and Muir, H. M. *Anal. Biochem.*, 4:330–334, 1962.

Brown, R. A. and Weiss, J. B. *Ann. Rheum. Dis.*, 47(11):881–885, 1988.

Budavari, S. Merck Index, 11th edition. Rahway, N.J.: Mereck & Co., Ltd., 1989.

Crum, R., Szabo, S., and Folkman, J. *Science*, 230:1375–1378, 1985.

Danishefsky, I. and Siskovic, E. *Carbohydr. Res.*, 16:199–205, 1971.

Denekamp, J. and Hobson, B. *Br. J. Cancer*, 46:711–720, 1982.

Fabian, I., Bleiberg, I., and Aronson, M. *Biochim. Biophys. Acta*, 544:69–76, 1978.

Florey, H. W., Poole, J. C. F., and Meek, G. A. *J. Path. Bact.*, 77:625–636, 1959.

Folkman, J. *Ann. Surg.*, 175:409–416, 1972.

Folkman, J., Langer, R., Linhardt, R. J., Haudenschild, C., and Taylor, S. *Science*, 221:719–725, 1983.

Folkman, J. *Adv. Cancer Res.*, 43:175–230, 1985.

Folkman, J. *J. Cancer Res.*, 46:467, 1986.

Folkman, J., Weisz, P. B., Joullie, M. M., Li, W. W., and Ewing, W. R. *Science*, 243:1490–1493, 1989.

Folkman, J. *J. Natl. Cancer Inst.*, 82:4–6, 1990.

Gartner, S. and Henkind, P. *Surv. Ophthal.*, 22:291–312, 1978.

Good, D. J., Polverini, P. J., Rastinejad, F., LeBeau, M. M., Lemons, R. S., Frazier, W. A., and Bouck, N. P. *Proc. Natl. Acad. Sci. USA*, 87:6624–6628, 1990.

Haynes, R. C. In: A. G. Gilman, T. W. Rall, A. S. Nies and P. Taylor (eds.), Goodman & Gilman's "The Pharmacological Basis of Therapeutics", pp. 1431–1462, Pergamen Press, USA. 1990.

Hiebert, L. M. and Jacques, L. B. *Thromb. Res.*, 8:195–204, 1976.

Hobson, B. and Denekamp, J. *Br. J Cancer*, 49:405–413, 1984.

Ingber, D. E., Madri, J. A., and Folkman, J. *Endocrinology*, 119:1768–1775, 1986.

Ingber, D., Fujita, T., Kishimoto, S., Sudo, K., Kanamaru, T., Brem, H., and Folkman, J. *Nature*, 348:555–557, 1990.
Jaffe, E. A., Nachmann, R. L., Becker, C. G., and Minick, C. R. *J. Clin. Invest.*, 52:2745–2752, 1973.
Langer, R., Brem, H., Falterman, K., Klein, M., and Folkman, J. *Science*, 193:70–72, 1976.
Lindahl, U., Backstrom, G., and Thunberg, L. *J. Bio. Chem.*, 258:9826–9830, 1983.
Mahadoo, J., Hiebert, L., an Jaques, L. B. *Thromb. Res.*, 12:79–90, 1977.
Moses, M. A. and Langer, R. *Biotechnology*, 9:630–634, 1991.
Naieum, M., Gerdes, J., Abdulaziz, Z. Sunderland, C. A., Ailington, M. J., Stein, H., and Mason, D. Y. *J. Immunol. Methods*, 50:145–160, 1982.
Penhaligon, M. and Campejohn, R. S. *J. Natl. Cancer Inst.*, 74:869–873, 1985.
Pino, R. M. *Cell Tissue Res*, 250:257–266, 1987.
Tannock, I. F. *Br. J Cancer*, 22:258–273, 1968.
Taylor, S. and Folkman, J. *Nature*, 297:307–312, 1982.
Sakamoto, N., Tamaka, N. G., Tohgo, A., and Ogawa, H. *Canc. J.*, 1:55–58, 1986.
Sakamoto, N. and Tanaka, N. G. *Canc. J.*, 2:9–16, 1988.
Schaefer, C., Lo Bue, J., and Gollub, S. *Proc. Soc. Exp. Biol. Med.*, 164:69–74, 1980.
Sharpe, R. J., Byers, H. R., Scott, C. F., Bauer, S. I., and Maione, T. E. *J. Natl. Cancer Inst.*, 82:848–853, 1990.
Stau, Th., Metzand, J., and Taugner, R. *Naunyn-Schmiedeberg's Arch. Pharmacol.*, 280:93–102, 1973.
Sugiura, K. and Stock, C. C. *Cancer Res.*, 15:38–51, 1955.
Swinscow, T. D. V. Statistics at Square One. p. 58. Bath, UK: British Medical Association, Mendip Press, 1980.
Van Rijn, J. L. M. L., Trillou, M., Mardiguian, J., Tobelem, G., and Caen, *J. Thromb. Res.*, 45:211–222, 1987.
Waltman, D. D., Gitter, K. A., Yannuzzi, L., and Schatz, H. *Am. J. Ophthal.*, 85:704–710, 1978.
West, D. & Kumar, S. Lancet, I, (8587) 715, 1988.
Ziche, M., Ruggerio, M., Pasquali, F., and Chiarugi, V. P. *Int J Cancer*, 35:549–552, 1985.

What is claimed is:

1. A conjugate comprising a polymer, said polymer is a heparin, conjugated to a selected steroidal agent or agents by means of a biologically releasable bond formed between a reactive group on the steroidal agent or agents and:
   a) a free amino group revealed on the polymer through removal of a sulfate, acetyl or acyl group or groups attached to said amino group;
   b) a free carboxyl group on the polymer;
   c) a reactive group derivatized onto the polymer; or
   d) a combination of a), b) or c);
wherein the conjugate is further characterized as having a molar ratio of agent/polymer of greater than 1 mole agent/mole of polymer.

2. The conjugate of claim 1, wherein the polymer derivative is a non-anticoagulating heparin derivative.

3. The conjugate of claim 2, wherein the conjugate has less than 2.5% of the anticoagulating activity of native heparin.

4. The conjugate of claim 1, wherein the polymer is derivatized to introduce functional groups permitting the attachment of the selected agent through a biologically releasable bond.

5. The conjugate of claim 4, wherein the polymer is derivatized to introduce functional groups permitting the attachment of the selected agent through a biologically releasable disulfide or trisulfide bond.

6. The conjugate of claim 1, wherein the biologically releasable bond is a selectively hydrolyzable bond.

7. The conjugate of claim 6, wherein the selectively hydrolyzable bond is an acid-labile bond.

8. The conjugate of claim 7, wherein the acid-labile bond is hydrolyzable at a pH of 4.8 or lower.

9. The conjugate of claim 7, wherein the polymer is derivatized to introduce side chains terminating in hydrazide, hydrazine, primary amine or secondary amine groups.

10. The conjugate of claim 9, wherein the derivatized polymer is the condensation product of the polymer and adipic dihydrazide, succinic dihydrazide, hydrazine or hydrazine hydrate, and the agent is conjugated to the polymer through a Schiff's base linkage.

11. The conjugate of claim 10, wherein the agent is conjugated to the polymer through a hydrazone or acyl hydrazone bond.

12. The conjugate of claim 11, wherein the agent is conjugated to the polymer through a hydrazide linker having the structure $$R\text{-CO-NH-NH}_2$$

wherein

R=the polymer,

13. The conjugate of claim 10, wherein the agent is conjugated to the polymer by a hydrazide linker having the structure:

$$R\text{-CO-NH-NH-CO-}(CH_2)_n\text{-CO-NH-NH}_2;$$

wherein n=1–50; and

R=the polymer.

14. The conjugate of claim 1, wherein the biologically releasable bond is an enzyme-sensitive bond.

15. The conjugate of claim 14, wherein the enzyme-sensitive bond is a peptide bond.

16. The conjugate of claim 15, wherein the agent is linked to the polymer through a peptide that includes the sequence Leu-Ala-Leu-Ala.

17. The conjugate of claim 14, wherein the enzyme-sensitive bond is an ester, an amide, a phosphodiester or a glycoside.

18. The conjugate of claim 1, wherein the steroidal agent is asteroid from Table II or Table IV.

19. The conjugate of claim 1, wherein the steroidal agent has anti-angiogenic activity.

20. The conjugate of claim 1, wherein the steroidal agent has anti-angiostatic activity.

21. A pharmaceutical preparation comprising the conjugate of claim 1 dispersed in a pharmacologically acceptable vehicle.

22. The pharmaceutical preparation of claim 21, suitable for parenteral administration.

23. The conjugate of claim 1, wherein the molar ratio of agent:polymer is at least 5 moles agent/mole polymer.

24. The conjugate of claim 1, wherein the molar ration of agent:polymer ranges from about 5 to about 80 moles agent/mole polymer.

* * * * *

UNITED STATES PATENT AND TRADEMARK OFFICE
CERTIFICATE OF CORRECTION

PATENT NO. : 5,474,765

DATED : December 12, 1995

INVENTOR(S) : Thorpe

It is certified that error appears in the above-identified patent and that said Letters Patent is hereby corrected as shown below:

In claim 2, column 35, lines 55 and 56, delete "derivative is a non-anticoagulating heparin derivative." and insert --is non-anticoagulating.-- therefor.

In claim 12, column 36, line 28, delete "polymer," and insert --polymer.-- therefor.

In claim 18, column 36, line 49, delete "asteroid" and insert --a steroid-- therefor.

In claim 24, column 36, line 61, delete "ration" and insert --ratio-- therefor.

Signed and Sealed this

Twenty-sixth Day of March, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.: 5,474,765

DATED: December 12, 1995

INVENTOR(S): Philip E. Thorpe

It is certified that error appears in the above-identified patent and that said Letters Patent is hereby corrected as shown below:

In the Abstract, line 9, delete "asteroid" and insert therefor --a steroid--.

In column 1, lines 13, 18 and 25, delete "asteroid" and insert therefor --a steroid--.

In column 3, lines 16 and 21, delete "asteroid" and insert therefor --a steroid--.

In column 5, line 57, delete "asteroid" and insert therefor --a steroid--.

In column 9, line 59, delete "asteroid" and insert therefor --a steroid--.

In column 10, lines 53 and 54, delete "aidehyde" and insert therefor --aldehyde--.

In column 11, lines 36 and 63, delete "asteroid" and insert therefor --a steroid--.

Signed and Sealed this

Thirty-first Day of December, 1996

Attest:

BRUCE LEHMAN

*Attesting Officer*      *Commissioner of Patents and Trademarks*